US009408899B2

(12) United States Patent
McLeod et al.

(10) Patent No.: US 9,408,899 B2
(45) Date of Patent: Aug. 9, 2016

(54) VACCINES AGAINST *TOXOPLASMA GONDII*

(75) Inventors: Rima McLeod, Chicago, IL (US); Tze Guan Tan, Cambridge, MA (US); Jeffery L. Alexander, San Diego, CA (US); Hua Cong, Shandong (CN); William H. Witola, Auburn, AL (US); Kamal El Bissati, Chicago, IL (US); Ernest J. Mui, Chicago, IL (US); Steven G. Reed, Bellevue, WA (US)

(73) Assignees: The University of Chicago, Chicago, IL (US); Infectious Disease Research Institute, Seattle, WA (US); Paxvax, Inc., San Diego, CA (US)

( * ) Notice: Subject to any disclaimer, the term of this patent is extended or adjusted under 35 U.S.C. 154(b) by 0 days.

(21) Appl. No.: 13/823,668

(22) PCT Filed: Nov. 3, 2011

(86) PCT No.: PCT/US2011/059147
§ 371 (c)(1),
(2), (4) Date: Mar. 14, 2013

(87) PCT Pub. No.: WO2012/061599
PCT Pub. Date: May 10, 2012

(65) Prior Publication Data
US 2013/0273094 A1 Oct. 17, 2013

Related U.S. Application Data

(60) Provisional application No. 61/456,309, filed on Nov. 4, 2010.

(51) Int. Cl.
*A61K 39/00* (2006.01)
*A61K 39/39* (2006.01)
*A61K 39/002* (2006.01)

(52) U.S. Cl.
CPC ..... *A61K 39/002* (2013.01); *A61K 2039/55572* (2013.01); *A61K 2039/6031* (2013.01)

(58) Field of Classification Search
None
See application file for complete search history.

(56) References Cited

U.S. PATENT DOCUMENTS

2004/0248113 A1 12/2004 Sette et al.
2009/0215087 A1 8/2009 Hill et al.

FOREIGN PATENT DOCUMENTS

FR WO2007125209 A1 * 11/2007 ............. C07K 14/45
WO WO 0143768 A2 * 6/2001

OTHER PUBLICATIONS

Tan et al. 2010 (Identification of T. gondii epitopes, adjuvants, and host genetic factors that influence protection of mice and humans; Vaccine 28:3977-3989).*

Tan et al. 2010 (Identification of T. gondii epitopes, adjuvants, and host genetic factors that influence protection of mice and humans; Vaccine; 28:3977-3989).*
Boothroyd 2009 (Toxoplasma gondii: 25 years and 25 major advances for the field; International Journal for Parasitology 39:935-946).*
Lekutis et al. 2000 (Toxoplasma gondii: Identification of a Developmentally Regulated Family of genes related to SAG2; Experimental Parasitology 96:89-96).*
Khan et al. 2009 (Selection at a Single Locus Leads to Widespread Expansion of Toxoplamsa gondii Lineages that are Virulent in Mice; PLoS Genetics 5(3):1-14).*
Alexander et al. 2000 (Linear PADRE T Helper Epitope and Carbohydrate B Cell Epitope Conjugates Induce Specific High Titer IgG Antibody Responses; The Journal of Immunology, 164:1625-1633).*
Sousa et al. 2009 (Selection of polymorphic peptides from GRA6 and GRA7 sequences Toxoplasma gondii strains to be used in serotyping; Clin Vaccine Immunol; 16(8):1158-69).*
Burg et al. 1989 (Direct and Sensitive Detection of a Pathogenic Protozoan, Toxoplasma gondii by Polymerase Chain Reaction; J Clin Microb 27(8): 1787-1792).*
Bui et al., "Development of an epitope conservancy analysis tool to facilitate the design of epitope-based diagnostics and vaccines," *BMC Bioinformatics*,8(361): 1-6 (2007).
Cheng et al., "Relationship Between the Inhibition Constant ($K_I$) and the Concentration of Inhibitor Which Causes 50 Per Cent Inhibition ($I_{50}$) of an Enzymatic Reaction," *Biochem. Pharmac.*, 22:3099-3108 (1973).
Cong et al., Human immunome, bioinformatic analyses using HLA supermotifs and the parasite genome, binding assays, studies of human T cell responses, and immunization of HLA-A*1101 transgenic mice including novel adjuvants provide a foundation for HLA-A03 restricted CD8 +T cell epitope based, adjuvanted vaccine protective against *Toxoplasma gondii, Immunome Res.*, 6(12): 1-15 (2010).
Cong et al., "Towards an immunosense vaccine to prevent toxoplasmosis: Protective *Toxoplasma gondii* epitopes restricted by HLA-A*0201," *Vaccine*, 29: 754-762 (2011).
Cong et al., "*Toxoplasma gondii* HLA-B*0702-restricted GRA720-28 peptide with adjuvants and a universal helper T cell epitope elicits CD8+T cells producing interferon-γ and reduces parasite burden in HLA-B*0702 mice," *Human Immunol.*, 73:1-10 (2012).
Dzierszinski et al., "Targeted disruption of the glycosylphosphatidylinositol-anchored surface antigen SAG3 gene in Toxoplasma gondii decreases host cell adhesion and drastically reduces virulence in mice," *Toxoplasma gondii SAG3 mutants*, 37(3): 574-582 (2000).

(Continued)

*Primary Examiner* — Gary Nickol
*Assistant Examiner* — Mary Lyons
(74) *Attorney, Agent, or Firm* — McDonnell Boehnen Hulbert & Berghoff LLP

(57) ABSTRACT

Vaccines are disclosed against parasites. The vaccines include peptides in an immunological composition. In particular, the parasite is *Toxoplas gondii*.

9 Claims, 11 Drawing Sheets

(56) References Cited

OTHER PUBLICATIONS

Gulukota et al., "Two Complementary methods for predicting peptides binding major histocompatibility complex molecules", *J. Mol. Biol.* 267: 1258-1267 (1997).

Henriquez et al., "Immunogenetics of *Toxoplasma gondii* Informs vaccine design", *Trends in Parasitology*, 26 (11): 550-555 (2010).

Hill et al., "Identification of a sporozoite-specific antigen from *Toxoplasma gondii*", *Toxoplasma Gondii Sporozoite Protein*, 97(2): 328-337 (2011).

Jung et al., "The SRS superfamily of *Toxoplasma* surface proteins," *International Journal for Parasitology*, 34: 285-296 (2004).

Kim et al., "Bradyzoite-specific surface antigen SRS9 plays a role in maintaining *Toxoplasma gondii* persistence in the brain and in host control of parasite replication in the intestine," *Infection and Immunity*, 75 (4): 1626-1634 (2007).

Kubo et al., "Definition of Specific Peptide Motifs for Four Major HLA-A Alleles[1]," *HLA-A Peptide Motifs*: 3913-3924 (1994).

Mercier et al., "Dense granules: Are they key organelles to help understand the parasitophorous vacuole of all apicomplexa parasites?," 35: 829-849 (2005).

Padilla et al., "Limited Role for CD4+T-cell help in the initial priming of Trypansoma cruzi-specific CD8+T cells," *Infection and Immunity*, 75 (1): 231-235 (2007).

Rapin et al., "Computational Immunology Meets Bioinformatics: The Use of Prediction Tools for Molecular Binding in the Simulation of the Immune System," *Computational Bioinformatics*, 5 (4): 1-14 (2010).

Saeij et al., "A cluster of four surface antigen genes specifically expressed in Bradyzoites, SAG2CDXY, plays an important role in *Toxoplasma gondii* persistence," *Infection and Immunity*, 76 (6): 2402-2410 (2008).

Sette et al., "The relationship between class 1 binding affinity and immunogenicity of potential cytotoxic T cell epitopes," *The Journal of Immunology*, 5586-5592 (1994).

Tan et al., "Identification of *T. gondii* epitopes, adjuvants, and host genetic factors that influence protection of mice and humans," *Vaccine*, 28: 3977-3989 (2010).

Vita et al., "The immune epitope Database 2.0," *Nucleic Acids Research*, 38:D854-D862 (2009).

Witola et al., "NALP1 Influences susceptibility to human congenital toxoplasmosis, proinflammatory cytokine response, and fate of *Toxoplasma gondii*-infected monocytic cells," *Infection and Immunity*, 79 (2): 756-766 (2011).

Search Report and Written Opinion issued in Int'l App. No. PCT/US11/59147 (2012).

* cited by examiner

| Lipopeptide Abbreviation | Peptide Sequence in Lipopeptide |
|---|---|
| LpKS9 | KSFKDILPK (SAG1*) |
| LpAM9 | AMLTAFFLR (GRA6*) |
| LpRS9 | RSFKDLLKK (GRA7*) |
| LpKS9/AM9/RS9 | KSFKDILPK (SAG1*)/ AMLTAFFLR (GRA6*)/ RSFKDLLKK (GRA7*) |

Lipopeptide HLA A03 Supertype Vaccine Constructs

Pam2Cys — PADRE ⋯ AAA — KSFKDILPK

Pam2Cys — PADRE ⋯ AAA — AMLTAFFLR

Pam2Cys — PADRE ⋯ AAA — RSFKDLLKK

Pam2Cys — PADRE — AAA — KSFKDILPK — AAA — AMLTAFFLR — AAA — RSFKDLLKK

FIG. 2A

SEQUENCE LISTING

<160> NUMBER OF SEQ ID NOS: 76

<210> SEQ ID NO 1
<211> LENGTH: 9
<212> TYPE: PRT
<213> ORGANISM: Toxoplasma gondii

<400> SEQUENCE: 1

Val Val Phe Val Val Phe Met Gly Val
1               5

```
<210> SEQ ID NO 2
<211> LENGTH: 9
<212> TYPE: PRT
<213> ORGANISM: Toxoplasma gondii

<400> SEQUENCE: 2

Phe Met Gly Val Leu Val Asn Ser Leu
1               5

<210> SEQ ID NO 3
<211> LENGTH: 9
<212> TYPE: PRT
<213> ORGANISM: Toxoplasma gondii

<400> SEQUENCE: 3

Phe Leu Val Pro Phe Val Val Phe Leu
1               5

<210> SEQ ID NO 4
<211> LENGTH: 9
<212> TYPE: PRT
<213> ORGANISM: Toxoplasma gondii

<400> SEQUENCE: 4

Lys Ser Phe Lys Asp Ile Leu Pro Lys
1               5

<210> SEQ ID NO 5
<211> LENGTH: 9
<212> TYPE: PRT
<213> ORGANISM: Toxoplasma gondii

<400> SEQUENCE: 5

Ala Met Leu Thr Ala Phe Phe Leu Arg
1               5

<210> SEQ ID NO 6
<211> LENGTH: 9
<212> TYPE: PRT
<213> ORGANISM: Toxoplasma gondii

<400> SEQUENCE: 6

Arg Ser Phe Lys Asp Leu Leu Lys Lys
1               5

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Lys Phe Val Ala Ala Trp Thr Leu Lys Ala Ala Ala
1               5                   10

<210> SEQ ID NO 8
<211> LENGTH: 9
<212> TYPE: PRT
<213> ORGANISM: Toxoplasma gondii

<400> SEQUENCE: 8

Leu Pro Gln Phe Ala Thr Ala Ala Thr
1               5
```

<210> SEQ ID NO 9
<211> LENGTH: 9
<212> TYPE: PRT
<213> ORGANISM: Toxoplasma gondii

<400> SEQUENCE: 9

Val Pro Phe Val Val Phe Leu Val Ala
1               5

<210> SEQ ID NO 10
<211> LENGTH: 10
<212> TYPE: PRT
<213> ORGANISM: Toxoplasma gondii

<400> SEQUENCE: 10

His Pro Gly Ser Val Asn Glu Phe Asp Phe
1               5                   10

<210> SEQ ID NO 11
<211> LENGTH: 9
<212> TYPE: PRT
<213> ORGANISM: Toxoplasma gondii

<400> SEQUENCE: 11

Phe Leu Ser Leu Ser Leu Leu Val Ile
1               5

<210> SEQ ID NO 12
<211> LENGTH: 10
<212> TYPE: PRT
<213> ORGANISM: Toxoplasma gondii

<400> SEQUENCE: 12

Phe Met Ile Ala Phe Ile Ser Cys Phe Ala
1               5                   10

<210> SEQ ID NO 13
<211> LENGTH: 9
<212> TYPE: PRT
<213> ORGANISM: Toxoplasma gondii

<400> SEQUENCE: 13

Phe Met Ile Val Ser Ile Ser Leu Val
1               5

<210> SEQ ID NO 14
<211> LENGTH: 9
<212> TYPE: PRT
<213> ORGANISM: Toxoplasma gondii

<400> SEQUENCE: 14

Phe Leu Thr Asp Tyr Ile Pro Gly Ala
1               5

<210> SEQ ID NO 15
<211> LENGTH: 9
<212> TYPE: PRT
<213> ORGANISM: Toxoplasma gondii

<400> SEQUENCE: 15

Phe Leu Leu Gly Leu Leu Val His Val
1               5

```
<210> SEQ ID NO 16
<211> LENGTH: 9
<212> TYPE: PRT
<213> ORGANISM: Toxoplasma gondii

<400> SEQUENCE: 16

Phe Val Ile Phe Ala Cys Asn Phe Val
1               5

<210> SEQ ID NO 17
<211> LENGTH: 9
<212> TYPE: PRT
<213> ORGANISM: Toxoplasma gondii

<400> SEQUENCE: 17

Ile Thr Met Gly Ser Leu Phe Phe Val
1               5

<210> SEQ ID NO 18
<211> LENGTH: 9
<212> TYPE: PRT
<213> ORGANISM: Toxoplasma gondii

<400> SEQUENCE: 18

Gly Leu Ala Ala Ala Val Val Ala Val
1               5

<210> SEQ ID NO 19
<211> LENGTH: 9
<212> TYPE: PRT
<213> ORGANISM: Toxoplasma gondii

<400> SEQUENCE: 19

Phe Ala Ala Ala Phe Phe Pro Ala Val
1               5

<210> SEQ ID NO 20
<211> LENGTH: 9
<212> TYPE: PRT
<213> ORGANISM: Toxoplasma gondii

<400> SEQUENCE: 20

Val Leu Leu Pro Val Leu Phe Gly Val
1               5

<210> SEQ ID NO 21
<211> LENGTH: 9
<212> TYPE: PRT
<213> ORGANISM: Toxoplasma gondii

<400> SEQUENCE: 21

Ser Thr Phe Trp Pro Cys Leu Leu Arg
1               5

<210> SEQ ID NO 22
<211> LENGTH: 9
<212> TYPE: PRT
<213> ORGANISM: Toxoplasma gondii

<400> SEQUENCE: 22

Ser Ser Ala Tyr Val Phe Ser Val Lys
1               5

<210> SEQ ID NO 23
<211> LENGTH: 10
```

<212> TYPE: PRT
<213> ORGANISM: Toxoplasma gondii

<400> SEQUENCE: 23

Ala Val Val Ser Leu Leu Arg Leu Leu Lys
1               5                   10

<210> SEQ ID NO 24
<211> LENGTH: 9
<212> TYPE: PRT
<213> ORGANISM: Toxoplasma gondii

<400> SEQUENCE: 24

Ser Thr Ser Pro Phe Ala Thr Arg Lys
1               5

<210> SEQ ID NO 25
<211> LENGTH: 10
<212> TYPE: PRT
<213> ORGANISM: Toxoplasma gondii

<400> SEQUENCE: 25

Ala Ser Thr Ser Pro Phe Ala Thr Arg Lys
1               5                   10

<210> SEQ ID NO 26
<211> LENGTH: 10
<212> TYPE: PRT
<213> ORGANISM: Toxoplasma gondii

<400> SEQUENCE: 26

Ala Ala Ala Ala Thr Pro Gly Leu Pro Lys
1               5                   10

<210> SEQ ID NO 27
<211> LENGTH: 9
<212> TYPE: PRT
<213> ORGANISM: Toxoplasma gondii

<400> SEQUENCE: 27

Ala Ala Ala Thr Pro Gly Leu Pro Lys
1               5

<210> SEQ ID NO 28
<211> LENGTH: 10
<212> TYPE: PRT
<213> ORGANISM: Toxoplasma gondii

<400> SEQUENCE: 28

Gly Val Pro Ala Val Pro Gly Leu Leu Lys
1               5                   10

<210> SEQ ID NO 29
<211> LENGTH: 10
<212> TYPE: PRT
<213> ORGANISM: Toxoplasma gondii

<400> SEQUENCE: 29

Ser Val Val Glu Glu Asn Thr Met Ala Lys
1               5                   10

<210> SEQ ID NO 30
<211> LENGTH: 10
<212> TYPE: PRT
<213> ORGANISM: Toxoplasma gondii

<400> SEQUENCE: 30

Ala Leu Leu Asp His Val Phe Ile Glu Lys
1               5                   10

<210> SEQ ID NO 31
<211> LENGTH: 9
<212> TYPE: PRT
<213> ORGANISM: Toxoplasma gondii

<400> SEQUENCE: 31

Ser Ser Pro Gln Asn Ile Phe Tyr Lys
1               5

<210> SEQ ID NO 32
<211> LENGTH: 10
<212> TYPE: PRT
<213> ORGANISM: Toxoplasma gondii

<400> SEQUENCE: 32

Ser Thr Thr Gly Val Gly Glu Thr Gly Lys
1               5                   10

<210> SEQ ID NO 33
<211> LENGTH: 9
<212> TYPE: PRT
<213> ORGANISM: Toxoplasma gondii

<400> SEQUENCE: 33

Gly Thr Glu Tyr Ser Leu Ala Leu Lys
1               5

<210> SEQ ID NO 34
<211> LENGTH: 9
<212> TYPE: PRT
<213> ORGANISM: Toxoplasma gondii

<400> SEQUENCE: 34

Ser Ser Pro Gln Asn Ile Phe Tyr Lys
1               5

<210> SEQ ID NO 35
<211> LENGTH: 10
<212> TYPE: PRT
<213> ORGANISM: Toxoplasma gondii

<400> SEQUENCE: 35

Ala Leu Leu Glu His Val Phe Ile Glu Lys
1               5                   10

<210> SEQ ID NO 36
<211> LENGTH: 9
<212> TYPE: PRT
<213> ORGANISM: Toxoplasma gondii

<400> SEQUENCE: 36

Ser Ser Ala Gln Thr Phe Phe Tyr Lys
1               5

<210> SEQ ID NO 37
<211> LENGTH: 9
<212> TYPE: PRT
<213> ORGANISM: Toxoplasma gondii

<400> SEQUENCE: 37

Thr Val Tyr Phe Ser Cys Asp Pro Lys
1               5

<210> SEQ ID NO 38
<211> LENGTH: 10
<212> TYPE: PRT
<213> ORGANISM: Toxoplasma gondii

<400> SEQUENCE: 38

Pro Ser Ser Ala Gln Thr Phe Phe Tyr Lys
1               5                   10

<210> SEQ ID NO 39
<211> LENGTH: 9
<212> TYPE: PRT
<213> ORGANISM: Toxoplasma gondii

<400> SEQUENCE: 39

Val Val Gly His Val Thr Leu Asn Lys
1               5

<210> SEQ ID NO 40
<211> LENGTH: 9
<212> TYPE: PRT
<213> ORGANISM: Toxoplasma gondii

<400> SEQUENCE: 40

Lys Gln Tyr Trp Tyr Lys Ile Glu Lys
1               5

<210> SEQ ID NO 41
<211> LENGTH: 10
<212> TYPE: PRT
<213> ORGANISM: Toxoplasma gondii

<400> SEQUENCE: 41

Thr Thr Cys Ser Val Leu Val Thr Val Lys
1               5                   10

<210> SEQ ID NO 42
<211> LENGTH: 10
<212> TYPE: PRT
<213> ORGANISM: Toxoplasma gondii

<400> SEQUENCE: 42

Ala Ala Ala Ser Val Gln Val Pro Leu Lys
1               5                   10

<210> SEQ ID NO 43
<211> LENGTH: 10
<212> TYPE: PRT
<213> ORGANISM: Toxoplasma gondii

<400> SEQUENCE: 43

Ala Ile Gln Ser Gln Lys Trp Thr Leu Lys
1               5                   10

<210> SEQ ID NO 44
<211> LENGTH: 10
<212> TYPE: PRT
<213> ORGANISM: Toxoplasma gondii

<400> SEQUENCE: 44

Thr Thr Arg Phe Val Glu Ile Phe Pro Lys 1               5                   10

<210> SEQ ID NO 45
<211> LENGTH: 9
<212> TYPE: PRT
<213> ORGANISM: Toxoplasma gondii

<400> SEQUENCE: 45

Val Ser Gly Ser Leu Thr Leu Ser Lys
1               5

<210> SEQ ID NO 46
<211> LENGTH: 10
<212> TYPE: PRT
<213> ORGANISM: Toxoplasma gondii

<400> SEQUENCE: 46

Thr Ser Ser Ala Tyr Val Phe Ser Val Lys
1               5                   10

<210> SEQ ID NO 47
<211> LENGTH: 10
<212> TYPE: PRT
<213> ORGANISM: Toxoplasma gondii

<400> SEQUENCE: 47

Tyr Val Phe Ser Val Lys Glu Leu Pro Lys
1               5                   10

<210> SEQ ID NO 48
<211> LENGTH: 9
<212> TYPE: PRT
<213> ORGANISM: Toxoplasma gondii

<400> SEQUENCE: 48

Lys Thr Glu Ala Thr Tyr Cys Tyr Lys
1               5

<210> SEQ ID NO 49
<211> LENGTH: 10
<212> TYPE: PRT
<213> ORGANISM: Toxoplasma gondii

<400> SEQUENCE: 49

Met Thr Leu Met Ile Thr Arg Asp Ser Lys
1               5                   10

<210> SEQ ID NO 50
<211> LENGTH: 9
<212> TYPE: PRT
<213> ORGANISM: Toxoplasma gondii

<400> SEQUENCE: 50

Val Val Ser Leu Leu Arg Leu Leu Lys
1               5

<210> SEQ ID NO 51
<211> LENGTH: 9
<212> TYPE: PRT
<213> ORGANISM: Toxoplasma gondii

<400> SEQUENCE: 51

Leu Thr Leu Thr Phe Ile Ser Thr Lys
1               5

<210> SEQ ID NO 52
<211> LENGTH: 9
<212> TYPE: PRT
<213> ORGANISM: Toxoplasma gondii

<400> SEQUENCE: 52

Ser Val Gln Leu Gly Ser Phe Asp Lys
1               5

<210> SEQ ID NO 53
<211> LENGTH: 9
<212> TYPE: PRT
<213> ORGANISM: Toxoplasma gondii

<400> SEQUENCE: 53

Ser Ala Val Trp Phe Gly Val Ala Lys
1               5

<210> SEQ ID NO 54
<211> LENGTH: 10
<212> TYPE: PRT
<213> ORGANISM: Toxoplasma gondii

<400> SEQUENCE: 54

Gly Val Met Thr Pro Asn Gln Met Val Lys
1               5                   10

<210> SEQ ID NO 55
<211> LENGTH: 9
<212> TYPE: PRT
<213> ORGANISM: Toxoplasma gondii

<400> SEQUENCE: 55

Leu Leu Ala Val Cys Met Ser Gly Val
1               5

<210> SEQ ID NO 56
<211> LENGTH: 10
<212> TYPE: PRT
<213> ORGANISM: Toxoplasma gondii

<400> SEQUENCE: 56

Phe Asn Met Asn Phe Tyr Ile Ile Gly Ala
1               5                   10

<210> SEQ ID NO 57
<211> LENGTH: 10
<212> TYPE: PRT
<213> ORGANISM: Toxoplasma gondii

<400> SEQUENCE: 57

Tyr Leu Gly Tyr Cys Ala Leu Leu Pro Leu
1               5                   10

<210> SEQ ID NO 58
<211> LENGTH: 10
<212> TYPE: PRT
<213> ORGANISM: Toxoplasma gondii

<400> SEQUENCE: 58

Lys Leu Met Arg Gln Tyr Asp Met Met Val
1               5                   10

<210> SEQ ID NO 59

```
<211> LENGTH: 9
<212> TYPE: PRT
<213> ORGANISM: Toxoplasma gondii

<400> SEQUENCE: 59

Arg Leu Gln Glu Ile Ile Ala Leu Ala
1               5

<210> SEQ ID NO 60
<211> LENGTH: 9
<212> TYPE: PRT
<213> ORGANISM: Toxoplasma gondii

<400> SEQUENCE: 60

Phe Leu Ala Gly Ser Gln Val Pro Gly
1               5

<210> SEQ ID NO 61
<211> LENGTH: 9
<212> TYPE: PRT
<213> ORGANISM: Toxoplasma gondii

<400> SEQUENCE: 61

Ser Leu Pro Leu Ser Pro Phe Thr Val
1               5

<210> SEQ ID NO 62
<211> LENGTH: 9
<212> TYPE: PRT
<213> ORGANISM: Toxoplasma gondii

<400> SEQUENCE: 62

Val Leu Ser Ser Ser Phe Met Ile Val
1               5

<210> SEQ ID NO 63
<211> LENGTH: 9
<212> TYPE: PRT
<213> ORGANISM: Toxoplasma gondii

<400> SEQUENCE: 63

Cys Leu Pro Leu Tyr Leu Phe Val Ile
1               5

<210> SEQ ID NO 64
<211> LENGTH: 9
<212> TYPE: PRT
<213> ORGANISM: Toxoplasma gondii

<400> SEQUENCE: 64

Phe Leu Val Gly Cys Ser Leu Thr Val
1               5

<210> SEQ ID NO 65
<211> LENGTH: 8
<212> TYPE: PRT
<213> ORGANISM: Toxoplasma gondii

<400> SEQUENCE: 65

Val Ser Gly Phe Val Val Ala Ser
1               5

<210> SEQ ID NO 66
<211> LENGTH: 10
<212> TYPE: PRT
```

<213> ORGANISM: Toxoplasma gondii

<400> SEQUENCE: 66

Lys Leu Met Ala Val Cys Ile Gly Gly Ile
1               5                   10

<210> SEQ ID NO 67
<211> LENGTH: 9
<212> TYPE: PRT
<213> ORGANISM: Toxoplasma gondii

<400> SEQUENCE: 67

Lys Leu Ala Asp Val Leu Pro Ser Ala
1               5

<210> SEQ ID NO 68
<211> LENGTH: 10
<212> TYPE: PRT
<213> ORGANISM: Toxoplasma gondii

<400> SEQUENCE: 68

Phe Leu Cys Asp Met Asp Ile Ala Thr Leu
1               5                   10

<210> SEQ ID NO 69
<211> LENGTH: 9
<212> TYPE: PRT
<213> ORGANISM: Toxoplasma gondii

<400> SEQUENCE: 69

Val Leu Ala Leu Ile Phe Val Gly Val
1               5

<210> SEQ ID NO 70
<211> LENGTH: 8
<212> TYPE: PRT
<213> ORGANISM: Toxoplasma gondii

<400> SEQUENCE: 70

Tyr Leu Gly Ser Gly Phe Ser Ala
1               5

<210> SEQ ID NO 71
<211> LENGTH: 9
<212> TYPE: PRT
<213> ORGANISM: Toxoplasma gondii

<400> SEQUENCE: 71

Met Met Pro Ser Gly Val Pro Met Ala
1               5

<210> SEQ ID NO 72
<211> LENGTH: 9
<212> TYPE: PRT
<213> ORGANISM: Toxoplasma gondii

<400> SEQUENCE: 72

Tyr Val Met Arg Tyr Ser Asp Tyr Val
1               5

<210> SEQ ID NO 73
<211> LENGTH: 12
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 73

Ala Ala Ala Lys Ser Phe Lys Asp Ile Leu Pro Lys
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Ala Ala Ala Met Leu Thr Ala Phe Phe Leu Arg
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Ala Ala Arg Ser Phe Lys Asp Leu Leu Lys Lys
1               5                   10

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Ala Ala Lys Ser Phe Lys Asp Ile Leu Pro Lys Ala Ala Ala Ala
1               5                   10                  15

Met Leu Thr Ala Phe Phe Leu Arg Ala Ala Ala Arg Ser Phe Lys Asp
            20                  25                  30

Leu Leu Lys Lys
            35
```

VACCINES AGAINST *TOXOPLASMA GONDII*

This application is a U.S. nationalization under 35 U.S.C. §371 of International Application No. PCT/US2011/059147, filed Nov. 3, 2011, which claims priority to Provisional Application No. 61/456,309, filed Nov. 4, 2010. The disclosures set forth in the referenced applications are incorporated herein by reference in their entireties.

This invention was made with Government support under U01 AI077887 awarded by The National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 30, 2011, is named 21459921.txt and is 12,384 bytes in size.

BACKGROUND

Toxoplasmosis refers to a disease caused by the parasite *Toxoplasma gondii* (*T. gondii*). The active infection destroys tissues, especially brain and eye in the fetus, newborn infant, immune compromised persons and those with retinal disease. In the presence of a normal immune response, the parasite remains as a chronic cryptic, latent brain infection, that can recrudesce and thus cause eye damage throughout the life of the host. About four thousand cases of newly active retinal disease are diagnosed in the U.S. each year. Importantly, this parasite chronically infects 30-50% of human population worldwide, with unknown consequences of this chronic infection of the brain in 2-3 billion persons throughout the world. Herein we describe various embodiments of an immunosense vaccine consisting of peptides created from immunogenic parasite proteins.

Human cells have a major histocompatibility complex (MHC) Class I processing pathway in which the proteasome in the cytosol degrades proteins from *T. gondii* into chains of eight to ten amino acids. These peptides associated with MHC Class I molecules then travel through the endoplasmic reticulum, and are presented at the surface of all cells so that the T cell receptors of cytotoxic T cells (CTLs) and IFN-γ producing CD8$^+$ T cells can recognize the MHC molecule and bound peptide. Thus, IFN-γ producing CD8$^+$ T cells are able to identify the peptides as self or non-self. Cells that present non-self peptides are killed and/or elicit IFN-γ. In this manner, CD8$^+$ T lymphocytes play a major role in protection against *T. gondii* by secreting IFN-γ which activates macrophages to inhibit replication, kill the parasite, and induce lysis of infected cells. Thus, this obligate intracellular parasite loses its intracellular niche.

Since CD8$^+$ T cells recognize target cells by peptide epitopes presented in the context of MHC Class I molecules, it is of great interest to identify MHC Class I restricted peptide epitopes from specific *T. gondii* antigens to facilitate creating vaccines that stimulate cell-mediated immune responses. The identification of CD8$^+$ T cell responses provides peptide antigens that can be used for directly monitoring CD8$^+$ T cell responses resulting from vaccination.

*Toxoplasma gondii* is an intracellular parasite which infects a broad range of mammalian hosts and can cause severe disease in immune-compromised or immunologically immature persons. The infection can cause severe ocular, neurologic, and systemic disease in these settings. Because no medicines eradicate all life cycle stages of this parasite, development of a vaccine against *T. gondii* is extremely useful, especially a vaccine that can prevent acquisition of parasite completely.

A preferred vaccine to protect against toxoplasmosis in humans includes epitopes that elicit a protective Th1 biased-immune response, characterized by the generation of long-lived IFN-γ-producing CD8$^+$ T cells. CD4$^+$ and CD8$^+$ T cells have a critical role in protective immunity to *T. gondii* in murine models and humans. CD8$^+$ T cells and interferon gamma (IFN-γ) are significant effectors mediating resistance to acute and chronic *T. gondii* infection. Peptide-based vaccines derived from CD8$^+$ T cell epitopes are a promising strategy to mobilize the immune system against *T. gondii* in humans. However, until now no *T. gondii* specific HLA restricted CD8$^+$ T cell epitopes that were proven to be protective had been identified.

SUMMARY

I. An Immunosense Vaccine to Prevent Toxoplasmosis: Protective *Toxoplasma gondii* Epitopes Restricted by HLA-A*0201

A vaccine to protect against toxoplasmosis in humans preferably includes antigens that elicit a protective T helper cell type 1 immune response, and generates long-lived IFN-γ-producing CD8$^+$ T cells. Herein, a predictive algorithm was utilized to identify candidate HLA-A02 supertype epitopes from *T. gondii* proteins. Thirteen peptides elicited production of IFN-γ from PBMC of HLA-A02 supertype persons seropositive for *T. gondii* infection, but not from seronegative controls. These peptides displayed high-affinity binding to HLA-A02 proteins. Immunization of HLA-A*0201 transgenic mice with these pooled peptides, with a universal CD4$^+$ epitope peptide called PADRE, formulated with adjuvant GLA-SE, induced CD8$^+$ T cell IFN-γ production and protected against parasite challenge. Peptides identified are useful in immunosense epitope-based vaccines.

HLA-A02 restricted epitopes from *T. gondii* have been identified. These epitopes have been evaluated as components in a candidate vaccine by immunizing HLA-A*0201 transgenic mice to determine whether they could provide protection against *T. gondii* challenge. The effect of adjuvants in poly-epitope immunizations has been evaluated for this supermotif immunosense vaccine. Accordingly, GRA10, GRA15, SAG2C, SAG2D, SAG2X, SAG3, SRS9, BSR4, SPA, and MIC proteins from *T. gondii* were screened for CD8$^+$ T cell epitopes by using an HLA motif algorithm in the immunoepitope database (IEDB). This was intended to predict potential epitopes that would bind to the HLA-A02 supertype family, which is present in 50% of the population worldwide, irrespective of ethnicity. Ten nonamer *T. gondii* derived peptides derived from the amino acid sequence of SAG2C$_{38-46}$, SAG2D$_{180-189}$, SAG2X$_{44-52}$, SAG2X$_{351-359}$, SAG3$_{136-144}$, SAG3$_{375-383}$, SPA$_{12-20}$, SPA$_{82-90}$, MIC1$_{9-17}$, and MICA2P$_{11-19}$ were identified via bioinformatic and affinity binding assays and tested in ELISpot assays with peripheral blood mononuclear cells from HLA-A*0201 *T. gondii*-seropositive individuals. SAG1, SUSA1, GRA2, GRA3, GRA6, GRA7, ROP2, ROP16, and ROP18 were also screened and GRA6$_{24-32}$ (VVFVVFMGV (SEQ ID NO: 1)), GRA6$_{29-37}$ (FMGVLVNSL (SEQ ID NO: 2)), and GRA3$_{25-33}$ (FLVPFVVFL (SEQ ID NO: 3)) also had been found to elicit IFN-γ from PBMC from seropositive but not seronegative persons (Tan T G et al., 2010). HLA-A*0201 transgenic mice immunized with the newly identified peptides, and the three HLA-A02 peptides identified previously were all pooled. They were administered with the CD4$^+$ helper T cell peptide PADRE and the adjuvant, GLA-SE, which induced high levels of IFN-γ production and protected mice against challenge from type II parasites.

II. Immunosense Based Vaccine Protects HLA-A*1101 Transgenic Mice Against Toxoplasmosis In another embodiment, a humanized HLA-A*1101 (an HLA-A03 supertype haplotype) transgenic mouse model was used to create/assess protective efficacy of a human CD8+ T cell epitope-based vaccine against primary *Toxoplasma gondii* infection. Peptide-based approaches to induce IFN-γ responses were evaluated to provide a foundation for development of immunosense vaccines for human use. Three immunodominant human CD8+ T-cell peptide epitopes, KSFKDILPK (SAG1$_{224-232}$) (SEQ ID NO: 4); AMLTAFFLR (GRA6$_{164-172}$) (SEQ ID NO: 5); RSFKDLLKK (GRA7$_{134-142}$) (SEQ ID NO: 6), were joined with a universal human CD4+ T cell peptide epitope PADRE (AKFVAAWTLKAAA (SEQ ID NO: 7)) to construct three separate pairs of CD4-CD8 lipopeptides or longer lipopeptides that linked the three peptides together. HLA-A*1101 transgenic mice were immunized with lipopeptides or a mixture of the peptides plus adjuvants, and T cell responses induced and protective efficacy were determined. Bioinformatic algorithms and binding studies identified additional CD8+ T cell peptides that elicited IFN-γ production by CD8+ T lymphocytes from HLA-A03 supertype donors. These peptides enhanced protection of HLA-A-1101 mice.

Peptide-based vaccines derived from CD8+ T cell epitopes are a promising strategy to mobilize the immune system against *T. gondii* in humans.

Three peptide epitopes from KSFKDILPK (SAG1$_{224-232}$) (SEQ ID NO: 4); AMLTAFFLR (GRA6$_{164-172}$) (SEQ ID NO: 5); and RSFKDLLKK (GRA7$_{134-142}$) (SEQ ID NO: 6) were identified to elicit IFN-γ from PBMCs of *T. gondii* from seropositive HLA-A03 supertype humans but not from PBMCs of *T. gondii* seronegative HLA-A03 supertype humans. (Tan, T. G., et al, 2010). Herein, 4 CD8+ T cell epitope containing vaccine formulations comprising lipopeptides that incorporate PADRE as well as an oil-in-water emulsion that includes a synthetic MLA derivative are described. The efficacy of various vaccine formulations consisting of the three CD8+ T cell peptides eliciting HLA-A*1101-restricted, CD8+ T cell-mediated IFN-γ production in vitro from HLA-A*1101 mice was examined.

Then, in order to identify additional peptides from *T. gondii* that are effective in eliciting IFN-γ from HLA-A03 supertype restricted CD8+ T cells, bioinformatic algorithms were utilized to identify additional, novel *T. gondii*-derived, CD8+ T cell epitopes restricted by the HLA-A03 supertype. The peptides from tachyzoite, bradyzoite and sporozoite proteins (GRA10, GRA15, SAG2C, SAG2D, SAG2X, SAG3, SRS9, BSR4, SPA, MIC) of the type II *T. gondii* strain, ME49, were screened searching for those with high binding scores in a bioinformatic analysis (IC$_{50}$<50 nM) and in binding assays. In addition, peripheral blood mononuclear cells from seropositive and seronegative persons were tested for response to these peptides using an IFN-γ ELISpot assay. These latter studies were used to identify other peptides for inclusion in a multi-epitope, next generation immunosense vaccine.

III. Immunization with a *Toxoplasma gondii* HLA-B*0702 Restricted GRA7$_{20-28}$ Peptide Plus Adjuvants Elicits IFN-γ from Human and Murine CD8+ T Cells and Protects HLA-B*0702 Mice Against Subsequent Parasite Challenge CD8+ T cells have been shown to act as cytolytic effectors and produce IFN-γ to mediate resistance to *Toxoplasma gondii* in murine models due to recognition of peptides restricted by murine MHC Class I molecules. However, no *T. gondii* specific HLA-B07 restricted peptides were proven protective against *T. gondii*. Recently, two *T. gondii*-specific HLA-B*0702-restricted T cell epitopes, GRA7$_{20-28}$ (LPQFATAAT (SEQ ID NO: 8)) and GRA3$_{27-35}$ (VPFVVFLVA (SEQ ID NO: 9)), displayed high-affinity binding to HLA-B*0702, and elicited IFN-γ from PBMCs of seropositive HLA-B*0702 persons. Herein, these peptides were evaluated to determine whether they could immunize and protect HLA-B*0702 transgenic mice when administered with adjuvants. Peptide-specific IFN-γ producing T cells were identified by ELISPOT and proliferation assays utilizing splenic T lymphocytes from HLA transgenic mice. When HLA-B*0702 mice were immunized with one of the epitopes identified, GRA7$_{20-28}$ in conjunction with a universal CD4+ T cell epitope (PADRE) and adjuvants (CD4+ T cell adjuvant, MLA, and TLR2 stimulatory Pam$_2$Cys for CD8+ T cells), this immunization induced CD8+ T cells to produce IFN-γ and protected mice against high parasite burden when challenged with *T. gondii*. This work demonstrates feasibility of immunosense approaches for identifying protective HLA-B*0702 restricted *T. gondii* peptides and adjuvants that elicit protective immune responses in HLA-B*0702 mice.

Herein, these peptides identified earlier using bioinformatics and in vitro analyses were evaluated as vaccine components administered in conjunction with pan DR epitope (PADRE), a universal helper T lymphocyte epitope in HLA-B*0702 transgenic mice. Immunization of HLA-B*0702 transgenic mice with the peptide LPQFATAAT (SEQ ID NO: 8) with the help of PADRE and MLA and Pam$_2$Cys as adjuvants activated CD8+ T cells to produce IFN-γ and protected against subsequent challenge with a high burden of a type II parasite.

Previously, HF10 (HPGSVNEFDF (SEQ ID NO: 10)), a single decapeptide, derived from the dense granule protein 6 (GRA6) was identified as the protective, immunodominant L$^d$-restricted epitope in H-2$^d$ mice infected with type II *T. gondii* parasite. This earlier work had reported that L$^d$ was essential for restriction of cyst number and brain pathology in L$^d$ mice. This also demonstrated that immunization of H-2L$^d$ mice with the lipopeptide constructed by HF10 and PADRE or HF10 with monophosphoryl lipid A (MLA) protected Balb/c mice. However, HF10 administered to HLA-B07 transgenic mice in a similar manner was not immunogenic despite a common L$^d$ and B7 peptide binding motif. Therefore, in order to find effective peptides for *T. gondii* derived HLA-B07+ restricted CD8+ T cells, bioinformatic algorithms were used to identify novel, *T. gondii*-derived, CD8+ T cell epitopes restricted by the HLA-B07 supertypes, which collectively provide coverage for 30% of the human population worldwide. The amino acid sequences from nine surface and secreted proteins (SAG1, SUSA1, GRA2, GRA3, GRA6, GRA7, ROP2, ROP16, ROP18) of the type II *T. gondii* strain, ME49, for HLA-B*0702-specific peptide binding scores were screened using bioinformatic analysis. Peripheral blood mononuclear cells from seropositive and seronegative persons were tested for response to these peptides using IFN-γ Elispot assay. Strikingly, two *T. gondii*-specific HLA-B*0702-restricted T cell epitopes, one derived from GRA7$_{20-28}$ (LPQFATAAT (SEQ ID NO: 8)), the other derived from GRA3$_{27-35}$ (VPFVVFLVA (SEQ ID NO: 9)) both displayed high-affinity binding to HLA-B*0702 and stimulated IFN-γ production by peripheral blood cells from HLA-B*0702 persons infected with *T. gondii*, but not seronegative controls.

BRIEF DESCRIPTION OF DRAWINGS

FIG. 1B discloses SEQ ID NOS 55-60, 12, 11, 61, 12-13, and 62, respectively, in order of appearance.

FIG. 2A. Schematic representation of the synthetic lipopeptide immunogens used. The C-terminal end of a promiscuous CD4⁺ T cell peptide epitope (PADRE) was joined in sequence with the N-terminal end of one of three different *T. gondii* CD8 T cell epitopes: SAG1$_{224-232}$ (A), GRA6$_{164-172}$ (B); GRA7$_{134-142}$ (C) or three epitopes linked together (D) with a three alanine linker. The N-terminal end of each resulting CD4-CD8 peptide was extended by a lysine covalently linked to one molecule of palmitic acid. This results in a four lipopeptides construct.

The abbreviation Lp is used herein to refer to the lipopeptide. When there is a mixture of components or undivided components they are named individually. Sequence of PADRE is AKFVAAWTLKAAA (SEQ ID NO: 7). Structure of Pam₂Cys is PAM₂KSS. FIG. 2A discloses the "Peptide Sequence in Lipopeptide" sequences as SEQ ID NOS 4-6 and 4-6, respectively, in order of appearance and the "Lipopeptide HLA A03 Supertype Vaccine Constructs" as SEQ ID NOS 73-76, respectively, in order of appearance.

DETAILED DESCRIPTION OF THE DISCLOSURE

I. Identification of HLA-A*0201-Restricted CD8⁺ T Cell Epitopes that Elicit IFN-γ from Seropositive Persons.

To identify candidate epitopes from *Toxoplasma gondii* that elicit IFN-γ from CD8⁺ T cells, the peptides derived from GRA10, GRA15, SAG2C, SAG2D, SAG2X, SAG3, SRS9, BSR4, SPA, and MIC were screened for potential supertype epitopes using the ARB, SMM, and ANN algorithms from immunoepitope database (IEDB) on the basis of their predicted binding affinity to HLA-A02 molecules. A total of 29 unique peptides $IC_{50} < 50$ nM of all ranked nonameric or decameric peptides were selected (Cong, et al., 2011).

Figure 1:
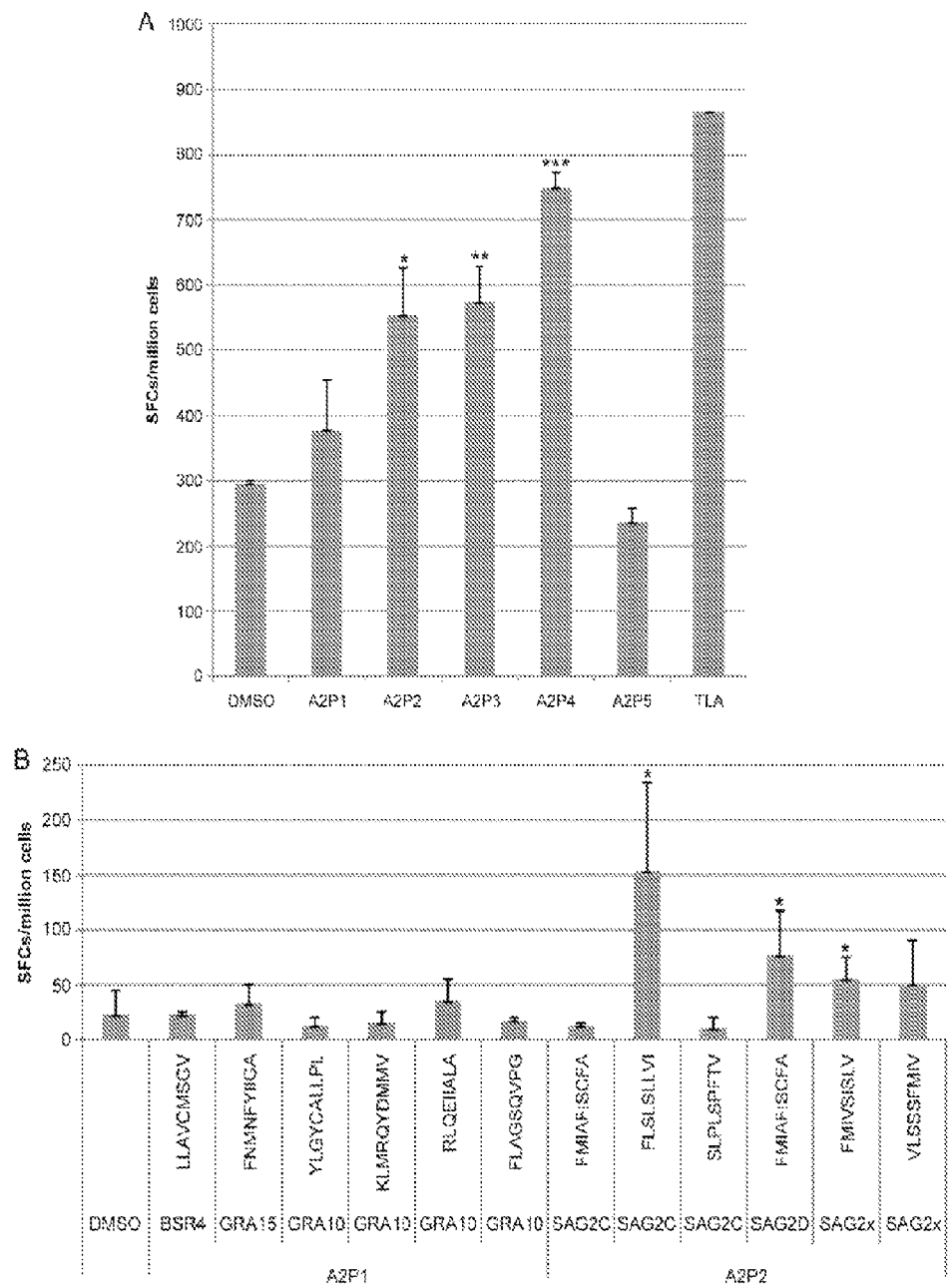
FIG. 1. IFN-γ ELISpot assay with pools of peptides that are predicted to bind avidly to HLA A02. (A) Twenty-nine HLA- A*02-restricted peptides were divided in 5 pools with 8 to 9 peptides per pool and tested for reactivity in PBMCs isolated from HLA-matched *T. gondii*-seropositive individuals in an ex vivo ELISpot assay. A2P1 to A2P5: peptide pools as described in Table 1. IFN-γ ELISpot assay with individual peptides in pool 1 and pool 2. DMSO, A2P2 ($p<0.05$); TLA, A2P1, A2P5 ($p>0.05$); A2P3 ($P<0.01$); A2P4 ($p<0.001$) (B) pool 3 and pool 4. FLSLSLLVI (SEQ ID NO: 11), FMIAFIS-CFA (SEQ ID NO: 12), FMIVSISLV (SEQ ID NO: 13) ($P<0.05$). (C) pool 5. FLTDYIPGA (SEQ ID NO: 14) ($p<0.05$); FLLGLLVHV (SEQ ID NO: 15) ($p<0.01$); FVI-FACNFV (SEQ ID NO: 16), ITMGSLFFV (SEQ ID NO: 17), GLAAAVVAV (SEQ ID NO: 18) ($p<0.001$). (D) that bind to HLA supertype HLA-A02 This graph shows the spot count of each peptide tested for reactivity in PBMCs isolated from HLA-A02 *T. gondii*-seropositive individuals. The peptides are listed by their sequence and antigen. FAAAFFPAV (SEQ ID NO: 19) ($p<0.05$); VLLPVLFGV (SEQ ID NO: 20) ($p<0.01$). *, $P<0.05$; $P<0.01$; *$P<0.001$.
Figure 1C:
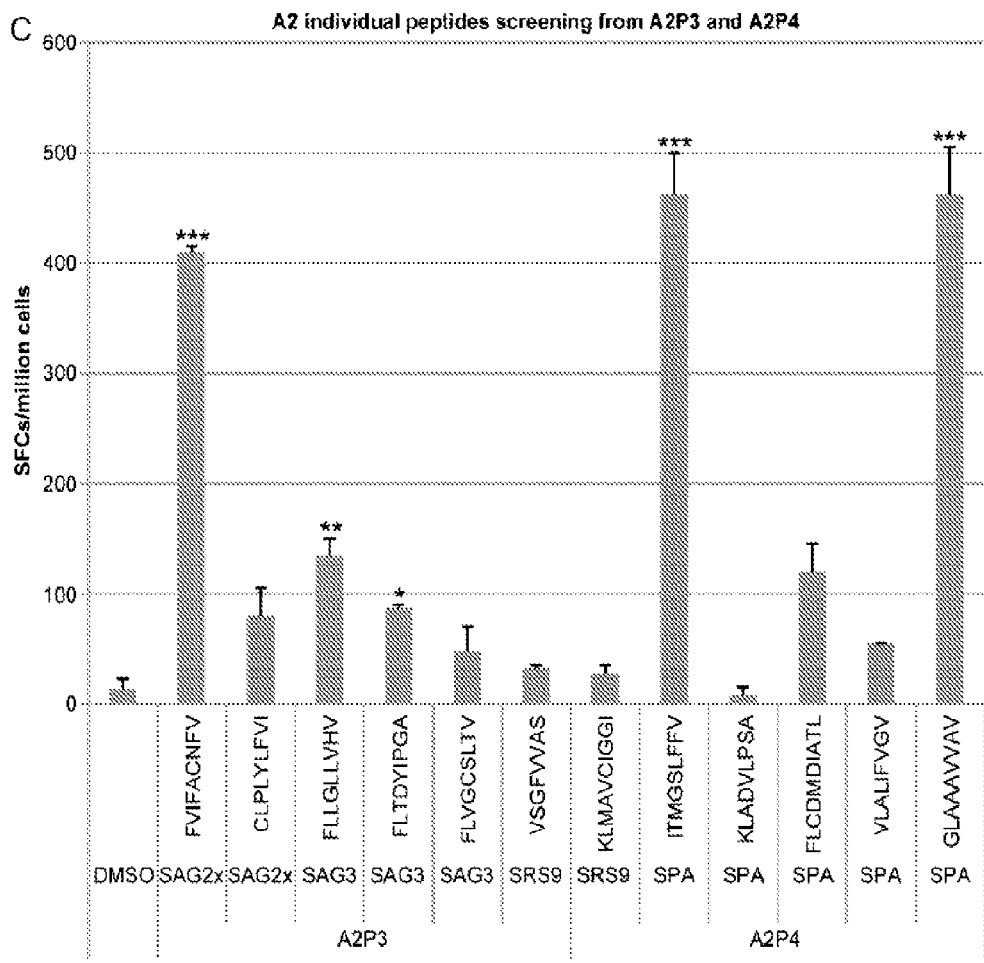
FIG. 1C discloses SEQ ID NOS 16, 63, 15, 14, 64-66, 17, 67-69, and 18, respectively, in order of appearance.
Figure 1D:
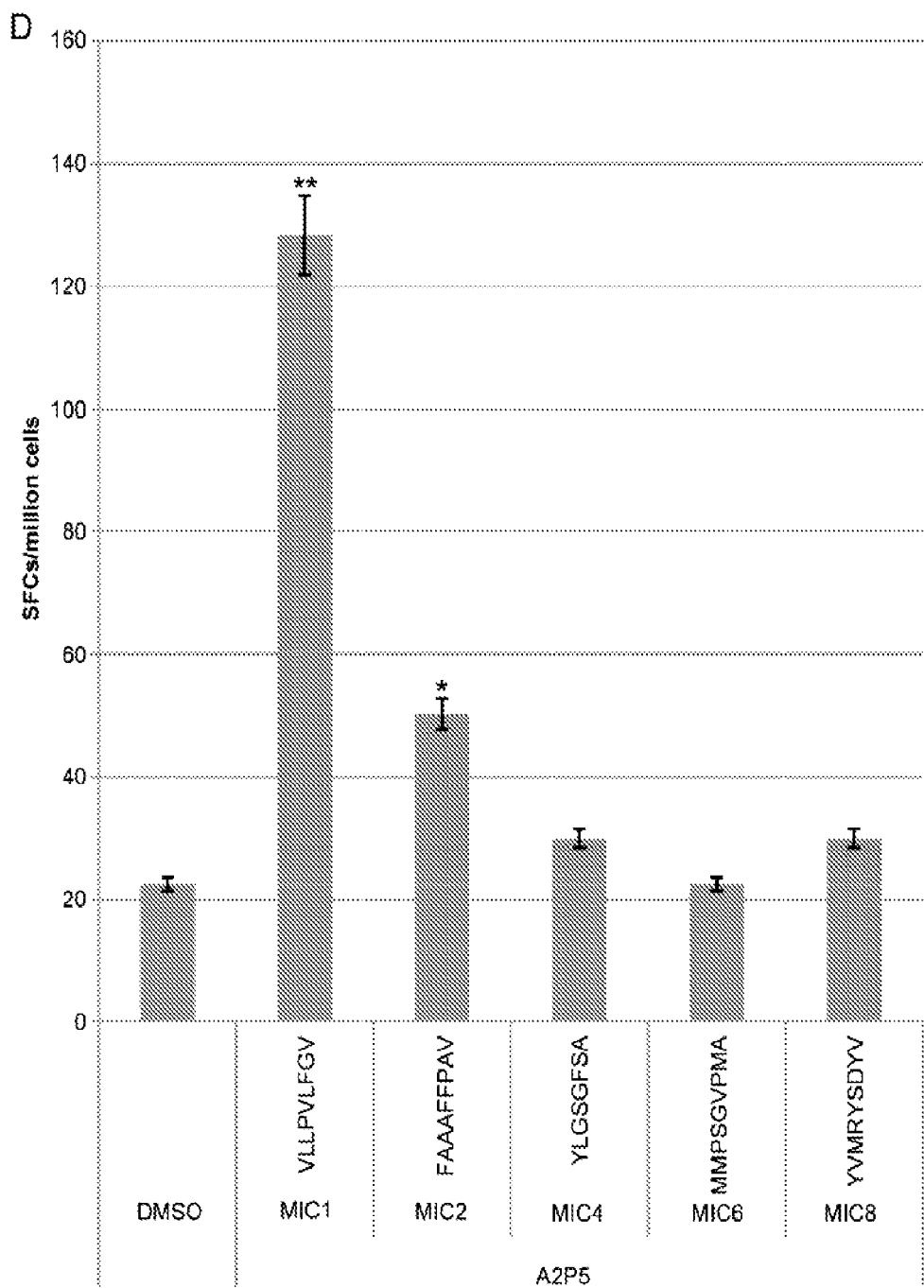
FIG. 1D discloses SEQ ID NOS 20, 19, and 70-72, respectively, in order of appearance.

To determine which of these peptides would be recognized in the context of a *Toxoplasma* infection, peripheral blood mononuclear cells from *T. gondii*-seropositive HLA-A*0201 individuals were tested for response to these peptides in pools or individually by using an IFN-γ ELISpot assay. Candidate peptides were considered immunogenic if they induced IFN-γ spot formation that was significant compared to an irrelevant HLA-A*0201-restricted peptide. As shown in FIG. 1A, there were three peptide pools which stimulated significant response by human peripheral blood mononuclear cells (PBMC) derived from HLA-A02 seropositive individuals. Then the ability of individual peptides in each of these peptide pools was tested to identify those that could stimulate significant T cell response by PBMC in HLA-A02 seropositive humans. Using this approach, 10 peptides were identified that were recognized by HLA-A02 PBMC from seropositive humans herein. These were: one from $SAG2C_{38-46}$ (FLSLSLLVI (SEQ ID NO: 11)); one from $SAG2D_{180-189}$ (FMIAFISCFA (SEQ ID NO: 12)); two from SAG2X ($SAG2X_{44-52}$, FVIFACNFV (SEQ ID NO: 16); 39-40$SAG2X_{351-359}$, FMIVSISLV (SEQ ID NO: 13)); two from SAG3 ($SAG3_{375-383}$, FLLGLLVHV (SEQ ID NO: 15); $SAG3_{136-144}$, FLTDYIPGA (SEQ ID NO: 14)); two from sporozoite antigen SPA ($SPA_{12-20}$, ITMGSLFFV (SEQ ID NO: 17); $SPA_{82-90}$, GLAAAVVAV (SEQ ID NO: 18); one from $MIC1_{9-17}$ (VLLPVLFGV (SEQ ID NO: 20)); and one from $MICA2P_{11-19}$ (FAAAFFPAV (SEQ ID NO: 19)). All these identified peptides stimulated significant IFN-γ production by peripheral blood cells from 4 HLA-A*0201 persons infected with *T. gondii*, but not from 4 seronegative controls.

MHC Binding Assay Demonstrates A2-Supertype Binding Capacity of Peptides Recognized by HLA A2 Positive PBMCs.

The binding affinity of these identified peptides for MHC A2 molecules was proven empirically with a MHC binding assay. All of the peptides identified herein were bound with high affinity to the HLA-A02, all binding 4 or more alleles within the respective supertype except one binding 2 alleles. There are nine out of ten peptides that have HLA-A*0201 binding affinity that bound with a $K_d$ of less than 50 nM. Specifically, $SAG2X_{44-52}$, $SAG2X_{351-359}$, $SPA1_{12-20}$, and $MICA2P_{11-19}$ bound with a $K_d$ of 50 nM or less for all five tested HLA-A02 alleles. $SAG3_{375-383}$, $SAG3_{136-144}$, SPA12-20, and $MIC1_{9-17}$ bound 4 HLA-A02 alleles with affinities under 50 nM. $SAG2C_{38-46}$ bound HLA-A*0201 with >50 nM affinity, but bound HLA-A*0202 and HLA-A*0203 allele in the 50 to 500 nM range (intermediate binding). The data shows that all these identified peptides bound proteins of the HLA-A02 supertype as predicted, which would be predictive of candidates for eliciting IFN-γ from CD8+ T cells.

CD8+ T Cell Responses Against Peptides After Immunization in HLA Transgenic Mice.

To determine whether the peptides identified were immunogenic in vivo, HLA-A*0201 transgenic mice were immunized with pools of peptides that included peptides identified above as well as three other CD8+ T-cell epitopes, VVFVVFMGV ($GRA6_{24-32}$) (SEQ ID NO: 1), FMGVLVNSL ($GRA6_{29-37}$) (SEQ ID NO: 2), and FLVPFVVFL ($GRA3_{25-33}$) (SEQ ID NO: 3). A summary of peptide binding and immunogenicity activity is provided in Table 1. HLA-A*0201 transgenic mice were immunized with; (1) CD8+ epitope peptide pools, (2) CD8+ epitope peptide pools plus PADRE, and (3) CD8+ epitope peptides pool plus PADRE emulsified with GLA-SE. Eleven to fourteen days post immuniztion, spleen cells were isolated and exposed to each individual peptide. A peptide was considered immunogenic if it induced IFN-γ spot formation that was significantly higher in the immunization group when compared with the group immunization with PBS. After the immunizations with the two pooled peptides, $SAG2C_{38-46}$ (FLSLSLLVI (SEQ ID NO: 11)) and $SAG2D_{180-189}$ (FMIAFISCFA (SEQ ID NO: 12)) stimulated T cells from immunized HLA-A*0201 transgenic mice to produce significant IFN-γ production in vitro. However, when PADRE, a universal CD4+ epitope peptide, was added to the immunizing peptides, five peptides ($SAG2C_{38-46}$ FLSLSLLVI (SEQ ID NO: 11); $SAG2D_{180-189}$ FMIAFISCFA (SEQ ID NO: 12); $SAG2X_{44-52}$ FVIFACNFV (SEQ ID NO: 16); $SAG2X_{351-359}$ FMIVSISLV (SEQ ID NO: 13); $SAG3_{375-383}$ FLLGLLVHV (SEQ ID NO: 15)) induced significant IFN-γ production from T cells of immunized mice. More strikingly, all peptides except $GRA6_{24-32}$ (VVFVVFMGV (SEQ ID NO: 1)) and $MICA2P_{11-19}$ (FAAAFFPAV (SEQ ID NO: 19)) were found to be immunogenic when MLA also was used as an adjuvant to immunize HLA-A*0201 mice. To assess relative contributions of CD8+ T cells to overal IFN-γ response, the activity of splenic CD8+ T cells was blocked using antibody specific to the CD8+ T cell receptor. IFN-γ spot formation was significantly reduced in the presence of antibody to CD8 incubated with the spleen cells from mice immunized with the pooled peptides plus PADRE and MLA when the cells were stimulated by all of the peptides except $GRA6_{24-32}$ and $MICA2P_{11-19}$.

Peptide Immunizations are Protective Against *Toxoplasma* Challenge in HLA-A*0201 Transgenic Mice.

The epitopes that were identified could confer protection against parasite challenge in HLA-A*0201 mice. Groups of HLA-A*0201 mice (n=5-9 mice per group) were immunized with peptide pools with PADRE emulsified in MLA. Mice injected with PBS served as controls. Ten days after the second immunization, mice were challenged with 10,000 type II Prugniaud (Pru) strain that expresses the Firefly luciferase (FLUC) gene and imaged at 7 days post-challenge using the in vivo imaging system (IVIS®; Xenogen, Alameda, Calif.) as previously described. Mice were imaged in ventral positions and photonic emissions were assessed using Living Image® 2.20.1 software (Xenogen). Data were presented as pseudocolor representations of light intensity and mean photons/s/region of interest (ROI). The number of luciferase expressing parasites in the immunized HLA-A*0201 mice was significantly reduced compared to the unimmunized mice. A majority, 4 of 5 (80%) mice immunized with the peptides plus PADRE emulsified in MLA adjuvant survived parasite challenge (One mouse died between days 7 and 9.). In contrast, only 1 of 5 (20%) unimmunized mice survived parasite challenge (Three mice died between days 7 and 9 and one mouse died between days 9 and 11).

Population Coverage Prediction

An algorithm was developed to calculate projected population coverage of a T cell epitope-based vaccine using MHC binding or T cell restriction data and HLA gene frequencies. This web based tool found by Vita R et al. (2010), was used to predict population coverage of these HLA-A02 epitope peptides based vaccines. The population coverage calculation results showed that the population coverage is varied in different regions: these peptides covered 23.82% population in Australia; 47.01% in Europe; 26.87% in North America; 39.29% in South America; 21.40% in North-East Asia; 12.35% in South-East Asia; 26.78% in Oceania; and 18.27% in Sub-Saharan Africa; and 40.36% for others. The average population coverage is 25.61%±13.31%

Discussion

Eleven *T. gondii* protein amino acid sequences were screened for CD8+ T cell epitopes by using an HLA motif algorithm to predict potential epitopes corresponding to the HLA-A02 supertype family, which is represented in 47% of the Europeans and 25% of the world population. Peptides were screened from tachyzoite, bradyzoite or sporozoite proteins which were either seen to elicit immune response or were known to be secreted and present in the cytoplasm and thus able to access the MHC Class I pathway. These proteins included GRA10, GRA15, SAG2C, SAG2D, SAG2X, SAG3, SRS9, BSR4, SPA, MIC1 or MICA2P of the type II *T. gondii* strain, ME49, whose sequences came from the ToxoDB website http://toxodb.org/toxo/. These peptides were further selected based on a high MHC allele binding score in a bioinformatic analysis ($IC_{50}$<50 nM). Ten nonamer or decamer peptides derived from the amino acid sequence of SAG2C, SAG2D, SAG2X, SAG3, SPA, MIC1, and MICA2P were identified via ELISpot assays with peripheral blood mononuclear cells from HLA-A*0201 *T. gondii*-seropositive individuals. In addition, we included three peptides for analysis that had earlier been identified from VVFVVFMGV ($GRA6_{24-32}$) (SEQ ID NO: 1), FMGVLVNSL ($GRA6_{29-37}$) (SEQ ID NO: 2), FLVPFVVFL ($GRA3_{25-33}$) (SEQ ID NO: 3). HLA-A*0201 transgenic mice immunized with these peptide pools plus adjuvant could induce peptide-specific high IFN-γ production and protect mice against challenge from type II parasites.

The peptide epitopes reported here to elicit IFN-γ are primarily derived from SAG2, SPA and MIC proteins of type II *T. gondii*. Sequence analysis demonstrated that the SAG1 related sequence (SRS) protein family that is expressed in a stage-specific manner is divided into two major branches, the SAG1-like sequence family and SAG2-like sequence family (Jung C et al., 2004). The tachyzoite surface is dominated by SAG2A, SAG3, SRS1, SRS2, and SRS3. Some of these proteins have been shown to be involved in invasion and attachment. SAG3 was considered as one member of the redundant system of *T. gondii* receptors that act as ligands mediating host cell recognition and attachment (Dzierszinski F. et al., 2000). Two peptides, FLLGLLVHV (SEQ ID NO: 15) and FLTDYIPGA (SEQ ID NO: 14), derived from $SAG3_{375-383}$ and $SAG3_{136-144}$ were identified as epitopes that elicit IFN-γ from CD8+ T cells. HLA-binding assay demonstrates that these two peptides have good binding affinity for the HLA-A*0201 supertype. Not only do they have a high binding affinity for HLA-A*0201 allele, but they also bound well to three or four other HLA-A02 alleles.

SAG2C, -D, -X, -Y, encoding bradyzoite surface molecules belonging to the SAG2 family are important for persistence of cysts in the brain. A significantly lower cyst number was seen in mice infected with Pru ΔSAG2CDXY parasites (Saeij et al., 2005). There was one peptide disclosed herein derived from $SAG2C_{38-46}$, one peptide derived from $SAG2D_{180-189}$, and two peptides derived from $SAG2X_{44-52}$ and $SAG2X_{351-359}$ that elicited IFN-γ production from CD8+ T cells from seropositive HLA-A02 individuals, but not seronegative HLA-A02 persons. HLA-binding assay demonstrated that these peptides have good binding affinity for five HLA-A02 alleles, except $SAG2C_{38-46}$ which only bound two alleles with affinity≤50 nM.

The complete life cycle of *T. gondii* encompasses both the sexual stage (sporozoite) and asexual stage (tachyzoite and bradyzoite). Of the three, the infective stage of *T. gondii*, sporozoites in oocysts are resistant and persist in the environment after excretion by cats. Sporulation creates highly infectious oocysts that have been linked to large scale outbreaks of toxoplasmosis. Sporozoite surface antigen (SPA) is the dominant surface coat protein expressed on the surface of sporozoites. Two peptides derived from this protein, $SPA_{12-20}$ and $SPA_{82-90}$, were found to have the ability to stimulate human CD8+ T cells to produce IFN-γ and bound with high affinity all the tested HLA-A02 supertype allele peptides.

MIC1-3 knockout *T. gondii* was considered as a good candidate for a vaccine against *T. gondii*-induced abortion in sheep and although MIC knockout parasites could be a vaccine, MICs have been found to be immunogenic in mice. Herein, two peptides $MIC1_{9-17}$ and $MICA2P_{11-19}$ which have high binding affinity for HLA-A02 supertype were identified as CD8+ T cell epitopes that could elicit IFN-γ from *T. gondii* seropositive HLA-A02 persons. However, $MICA2P_{11-19}$ was not found to be immunogenic in HLA-A*0201 transgenic mice even when GLA-SE was used as an adjuvant.

The relationship between A2 binding affinity and the immunogenicity of a series of A2 motif-containing peptides has been examined previously (Sette et al. 1994; Rapin et al. 2010; Kubo et al. 1994). MHC affinity plays an important role in determining immune responsiveness. Only peptides with a relatively high binding affinity for MHC of 500 nM or less usually are immunogenic. All the identified peptides have binding affinities lower than 500 nM with 11 out of 13 peptides exhibiting very high A2 binding affinities.

Furthermore, epitopes selected from many gene products increase the breadth of the immune response. The combination of more epitopes from different proteins can make immunization more robust and broaden its coverage. Inclusion of epitopes derived from bradyzoites and sporozoites can control against bradyzoites from cysts or against sporozoites from oocysts early during acquisition of infection. T cells effective against bradyzoite epitopes can reduce number of bradyzoites immediately upon cyst rupture. Thus, these enhance the biologically relevant efficacy in humans as well as reach higher population coverage.

These peptides were proven to be immunogenic when these peptides were formulated with a universal CD4+ peptide, PADRE and adjuvants for immunization of HLA-A*0201 transgenic mice. PADRE, a synthetic nonnatural Pan HLA DR binding epitope peptide that binds promiscuously to variants of the human MHC Class II molecule DR and murine Class II, and is effective in human and HLA transgenic mice, can augment CD8+ T cell effector functions by inducing CD4+ T helper cells. Spleen cells from mice immunized with peptides alone cannot activate T cells to secrete IFN-γ, but when the CD4+ T helper cell epitope PADRE was added in the immunogen, the secretion of peptide-specific IFN-γ was elicited. This indicated that the PADRE epitope delivers help for a MHC Class I restricted peptide-specific CTL response to *T. gondii*. Our results suggest that in a vaccine to prevent *T. gondii* infection, both CD4+ and CD8+ epitopes are preferably be targeted in order to drive a protective immune response.

However, low-molecular-weight synthetic peptide antigens are not highly immunogenic by themselves. 3-deacylated monophosphoryl lipid A (GLA-SE) is a detoxified derivative of the lipopolysaccharide (LPS) from *Salmonella minesota* R595, which is a Toll-like receptor 4 (TLR4) agonist and thus a potent activator of Th1 responses. A robust response was observed when MLA was included in this preparation used to immunize mice. High amounts of IFN-γ production were elicited from mice immunized with pooled peptides plus PADRE and MLA when the spleen cells were stimulated by the individual peptides, and the immunized mice were subsequently protected against high parasite burden with type II parasite challenge and had a significantly enhanced survival rate.

Disclosures herein provide not only a conceptual foundation, but reagents and proof of principle in terms of protection.

Focus included the identification of HLA-A02-specific epitopes by selecting and testing peptides based on HLA-A*0201 binding motif. Thirteen peptides were identified via ELISpot assays with peripheral blood mononuclear cells from HLA-A02 seropositive persons. Eleven peptides with the help of CD4+ T cell epitopes and adjuvancy of GLA-SE were proven to be immunogenic in transgenic mice using an assay measuring ability to elicit IFN-γ and protect the mice against parasite challenge.

Construction of CD4-CD8 Peptides Based Candidate Vaccine

CD8+ T cell epitopes were identified from *Toxoplasma gondii* proteins, based on their significant recognition by T cells from *T. gondii* seropositive HLA-A*1101 individuals. A universal CD4+ T cell epitope, PADRE (AKFVAAWTLKAAA (SEQ ID NO: 7)), was linked in sequence with the N-terminal end of one of the three different *T. gondii* CD8+ T cell epitopes: KSFKDILPK ($SAG1_{224-232}$) (SEQ ID NO: 4), AMLTAFFLR ($GRA6_{164-172}$) (SEQ ID NO: 5), RSFKDLLKK ($GRA7_{134-142}$) (SEQ ID NO: 6) and these three epitopes linked together with three alanines as the linker. The N-terminal end of each resulting CD4-CD8 peptide was extended by a lysine covalently linked to two molecules of the palmitic acid moiety. The lipopeptides (Lp) were named as LpKS9, LpAM9, LpRS9 and LpKS9/AM9/RS9 which are shown in FIG. 2.

Immunogenicity of Lipopeptides in HLA-A*1101 Transgenic Mice

Figure 2B:
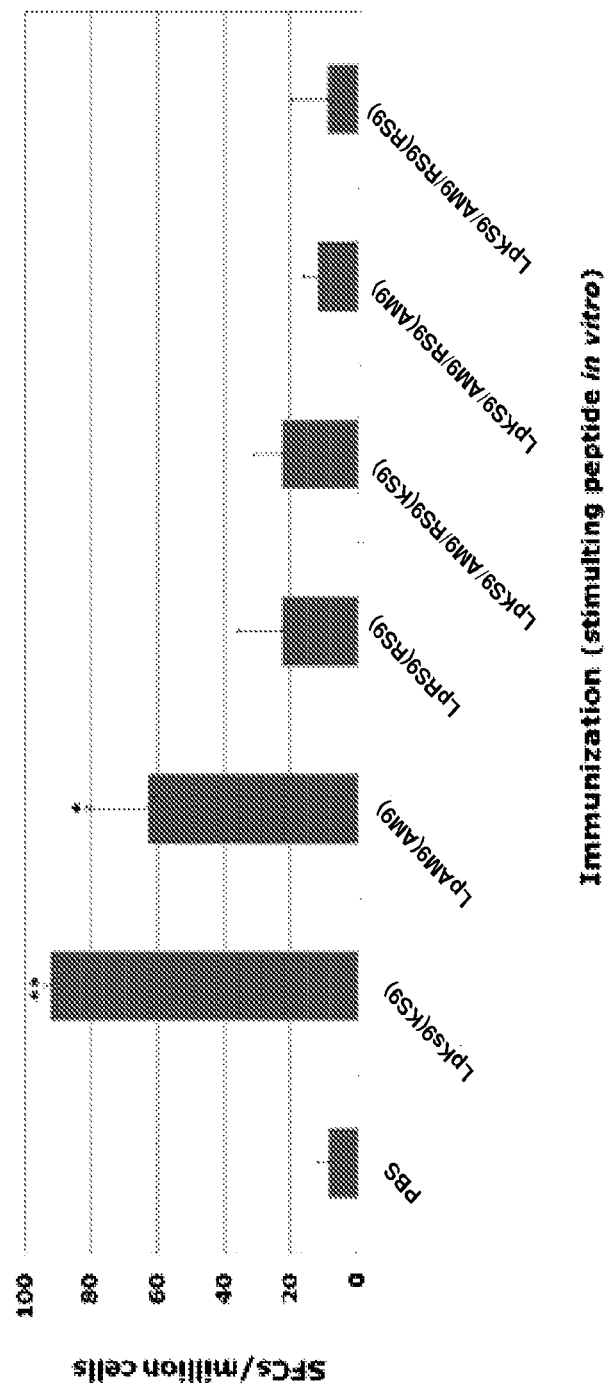
FIG. 2B. HLA-A*1101 mice immunized with lipopeptides. Mice were immunized with lipopeptides: LpKS9, LpAM9, LpRS9 and LpKS9/AM9/RS9. The mice were immunized twice at three week intervals. Ten to fourteen days after the last immunization, spleen cells were separated from immunized mice and stimulated by appropriate peptides in an ex vivo IFN-γ ELISpot assay. Data presented are averages of three independent replicate experiments. *, $P<0.05$; **, $P<0.01$.

HLA-A*1101 transgenic mice were immunized twice at three week intervals with lipopeptides which were dissolved in PBS. Two weeks after the last immunization, the spleens were removed from immunized mice and the ability of splenocytes to produce IFN-γ upon the stimulation of peptides was analyzed. Transgenic mice immunized with the three single peptide lipopeptide vaccines had T cells that produced IFN-γ (FIG. 2B). The lipopeptide vaccine LpKS9 and LpAM9 stimulated higher IFN-γ production than LpRS9. However, LpKS9/AM9/RS9 with three peptide epitopes linked together did not stimulate strong IFN-γ responses when splenocytes from these mice were exposed to each of the individual peptides in vitro.

Comparison of Vaccination with Different Formulations of Peptides

In order to determine which formulation was most immunogenic, vaccination with a single peptide or a mixture of the peptides was compared with linked lipopeptide vaccines. Mice immunized with a vaccine formulated with a single peptide $SAG^1_{224-232}$, KS9/PADRE with the adjuvancy of MLA and $Pam_2Cys$, elicited IFN-γ production (SFC:248±65; mean±SEM) four-fold higher (p<0.01) than mice that received LpKS9/MLA vaccination (63±17). Similar results, with substantial IFN-γ production, were found when splenocytes from mice immunized with a mixture of peptides and adjuvants which were compared with IFN-γ production by splenocytes from mice immunized with lipopeptide vaccines constructed with the three peptides linked together with alanine spacers LpKS9/AM9/RS9. However, significant IFN-γ production was only present with KS9 and AM9 stimulation of spleen cells, and was not present when the spleen cells were stimulated by RS9 peptide.

Effects of Adjuvant on Immunogenicity of Pooled Peptide Vaccination

To determine how adjuvants effected immunogenicity of these peptides, HLA-A*1101 transgenic mice were immunized with pools of peptides that included all of the three peptides (KS9, AM9, RS9) alone or with varying adjuvants. HLA-A*1101 transgenic mice were immunized with: (1) CD8+ epitope peptide pool, (2) peptide pool plus PADRE, (3) peptide pool plus PADRE emulsified with MLA, and (4) peptide pool plus PADRE and $Pam_2Cys$ emulsified with MLA. Mice were inoculated three times at two weeks intervals. Eleven to fourteen days post immunization, spleen cells were isolated and exposed to each individual peptide. A peptide was considered immunogenic if it induced IFN-γ spot formation that was significantly higher in the immunization group compared with the group inoculated with PBS. After the immunizations, only KS9, AM9 were found to be immunogenic in HLA-A*1101 transgenic mice when the CD4+ helper T cell peptide epitope was included. Robust responses were observed when MLA was added in the vaccine. Greater responses were elicited when $Pam_2Cys$ was used as an adjuvant for some but not all the peptides.

Vaccination with Peptide Pools and Adjuvants Protects Mice Against Type II Parasite Challenge HLA-A*1101 transgenic mice were immunized with peptide pools plus PADRE and $Pam_2Cys$ in MLA three times at two week intervals because it was the most immunogenic. Mice were challenged 2 wks after the last immunization. They were imaged 7 days post-challenge with 10,000 Pru (Fluc) using the Xenogen in vivo imaging system. The numbers of luciferase expressing parasites in immunized HLA-A*1101 transgenic mice were significantly reduced compared to the numbers of parasites in unimmunized mice.

Identification of New Candidate *T. gondii* Specific HLA-A*1101-Restricted Epitopes Three epitopes were identified that provided protection against parasite challenge. As a next generation vaccine additional HLA-A11 epitopes were identified to be used for vaccine development. In order to identify additional peptides from *T. gondii* that were present in tachyzoites, bradyzoites, and sporozoites of Type II strains for HLA-A03 supertype restricted CD8+ T cells, candidate peptides were screened from tachyzoite, bradyzoite and sporozoite proteins (GRA15, GRA10, SAG2C, SAG2X, SAG3, SRS9, SPA and MIC) of the Type II *T. gondii* strain (Table 2a). Peripheral blood mononuclear cells from seropositive *T. gondii* donors were tested for response to these peptides by using the IFN-γ ELISpot assay. Pooled peptides were tested initially and Pools 2 and 5 were significantly different (p<0.05) from the control. Then the individual peptides were tested. Three out of 34 epitopes elicited responses greater than 50 IFN-γ SFC from seropositive donors PBMC cells. They are derived from STFWPCLLR ($SAG2C_{13-21}$) (SEQ ID NO: 21); SSAYVFSVK ($SPA_{250-258}$) (SEQ ID NO: 22); and AVVSLLRLLK ($SPA_{89-98}$) (SEQ ID NO: 23). All peptides identified herein show high binding affinity to three to five HLA-A03 supertype alleles in the MHC-peptide binding assay (Table 2b).

Vaccination with Peptide Pools Including Newly Identified Peptides and Adjuvants Provide More Protection to Mice Against Type II Parasite Challenge HLA-A*1101 transgenic mice were immunized with peptide pools that include: KSFKDILPK ($SAG1_{224-232}$) (SEQ ID NO: 4); AMLTAFFLR ($GRA6_{164-172}$) (SEQ ID NO: 5); RSFKDLLKK ($GRA7_{134-142}$) (SEQ ID NO: 6); STFWPCLLR ($SAG2C_{13-21}$) (SEQ ID NO: 21); SSAYVFSVK ($SPA_{250-258}$) (SEQ ID NO: 22); AVVSLLRLLK ($SPA_{89-98}$) (SEQ ID NO: 23) plus PADRE and $Pam_2Cys$ in MLA three times at two week intervals. Significant IFN-γ spot formation responses were observed in vitro by the cells from immunized mice exposed to all the peptides except GRA7$_{134-142}$. The inclusion of the newly identified peptides thus had potential to enhance immunogenicity in transgenic HLA-A*1101 mice.

Mice were challenged 2 weeks after the last immunization. They were imaged five days post-challenge with 10,000 Pru (Fluc) using Xenogen in vivo imaging system. The numbers of luciferase expressing parasites in immunized HLA-A*1101 mice were significantly reduced compared to the numbers of parasites in unimmunized mice.

Population Coverage Prediction

An algorithm was developed to calculate projected population coverage of a T cell epitope-based vaccine using MHC binding or T cell restriction data and HLA gene frequencies. This web-based tool, (Vita R, Zarebski L, Greenbaum J A, Emami H, Hoof I, Salimi N, Damle R, Sette A, Peters B. The immune epitope database 2.0. Nucleic Acids Res. 2010 January; 38(Database issue):D854-62. Epub 2009 Nov. 11), was used to predict population coverage of these HLA-A*03 supertype peptide epitopes-based vaccine. The population coverage calculation results indicate that such coverage is varied in different geographic regions: these peptides covered 28.90% population in Australia; 41.46% in Europe; 11.29% in North America; 18.86% in North-East Asia; 36.62% in South-East Asia; 37.73% in South-East Asia; 34.29% in South-West Asia; 34.09% in Oceania; 27.32% in North Africa; 13.14% in Sub-Saharan Africa and 22.13% for others. The average population coverage is 24.51%±12.06%.

Discussion

Immunization of HLA-A*1101 transgenic mice with either mixture of peptides or lipopeptides derived from three identified *T. gondii* specific HLA-A*1101 restricted CD8$^+$ T cell epitopes emulsified in 3-deacylated monophosphoryl lipid A (MLA) adjuvant was evaluated. Immunization of transgenic mice with a mixture of CD8$^+$ epitope peptide pools plus PADRE and adjuvants were able to induce splenocyte to produce IFN-γ to protect against challenge with high burden of Type II parasite.

Conjugation of CD8$^+$ T cell determinants to lipid groups is known to enhance specific cell-mediated responses to target antigens in animals and humans, although mechanisms whereby immunity is achieved remains poorly understood. Lipopeptides hold several advantages over other conventional vaccine formulations; for instance, they are self-adjuvanting and display none of the toxicity-associated side effects of other Th1-inducing adjuvant systems. In the present disclosure, transgenic mice that were immunized with three short lipopeptide vaccines had T cells that produced IFN-γ. Among them the lipopeptide vaccine formulated with KS9 or AM9 stimulated higher IFN-γ production than the lipopeptide vaccine formulated with RS9. However, the lipopeptides with three epitope peptides linked together with alanine spacers did not stimulate an IFN-γ response by splenocytes from immunized mice when the splenocytes subsequently were exposed to each of the peptides in vitro. The reason why the lipopeptides with the three linked peptides did not work well in the transgenic mice might be related to the linker. The three linker "AAA" between the peptides had previously been demonstrated to result in sensitization to each of the linked peptides.

Figure 3:
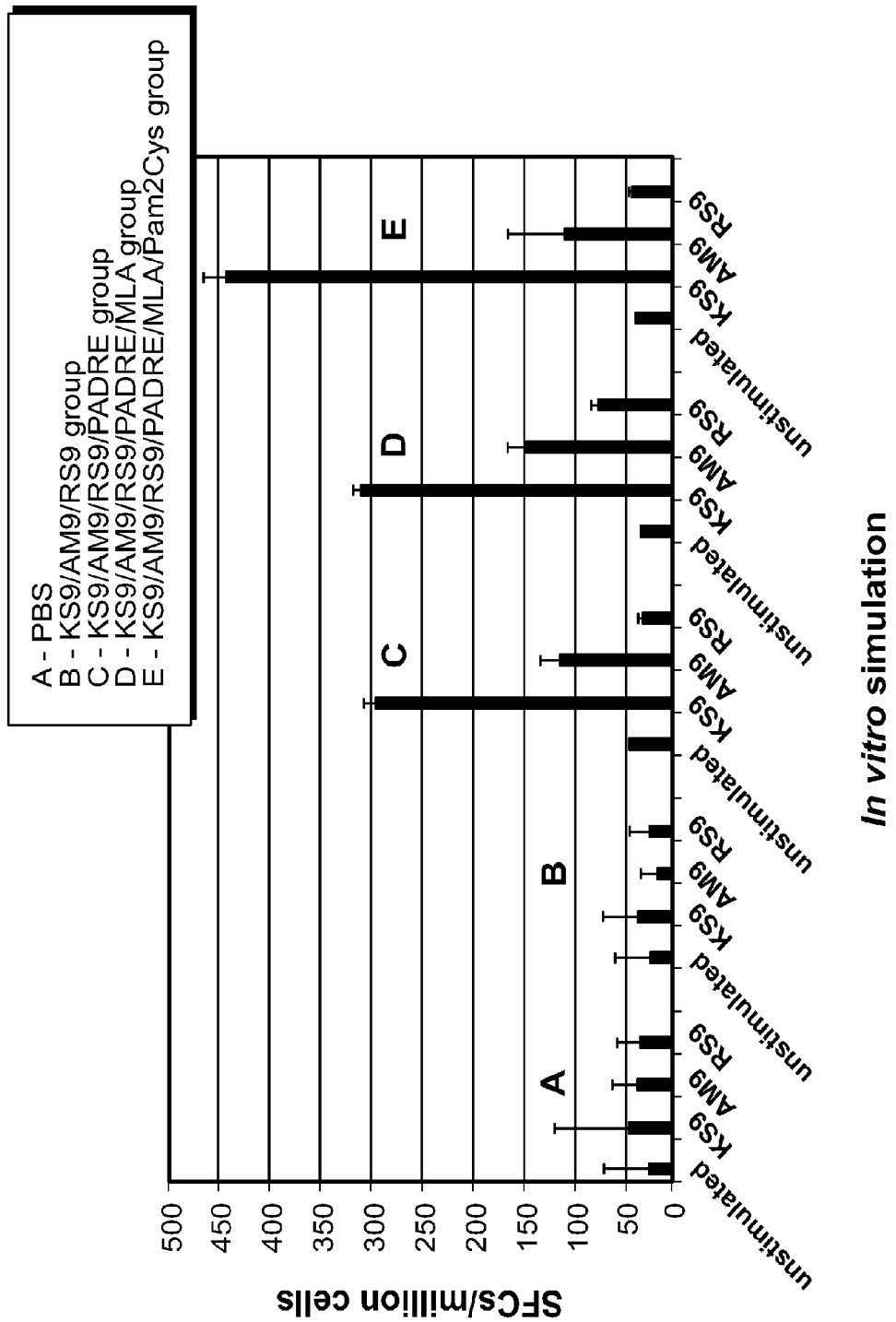
FIG. 3. HLA-A*1101 transgenic mice were immunized with peptide pool and adjuvants. Mice were immunized with (A) PBS, (B) peptide pool, (C) peptide pool with PADRE, (D) peptide pool with PADRE in GLA-SE, (E) peptide pool with PADRE and Pam2Cys in GLA-SE. Splenic T cells were isolated 10-14 days post-immunization and exposed to each peptide in an ex vivo IFN-g ELISpot assay.
Figure 4:
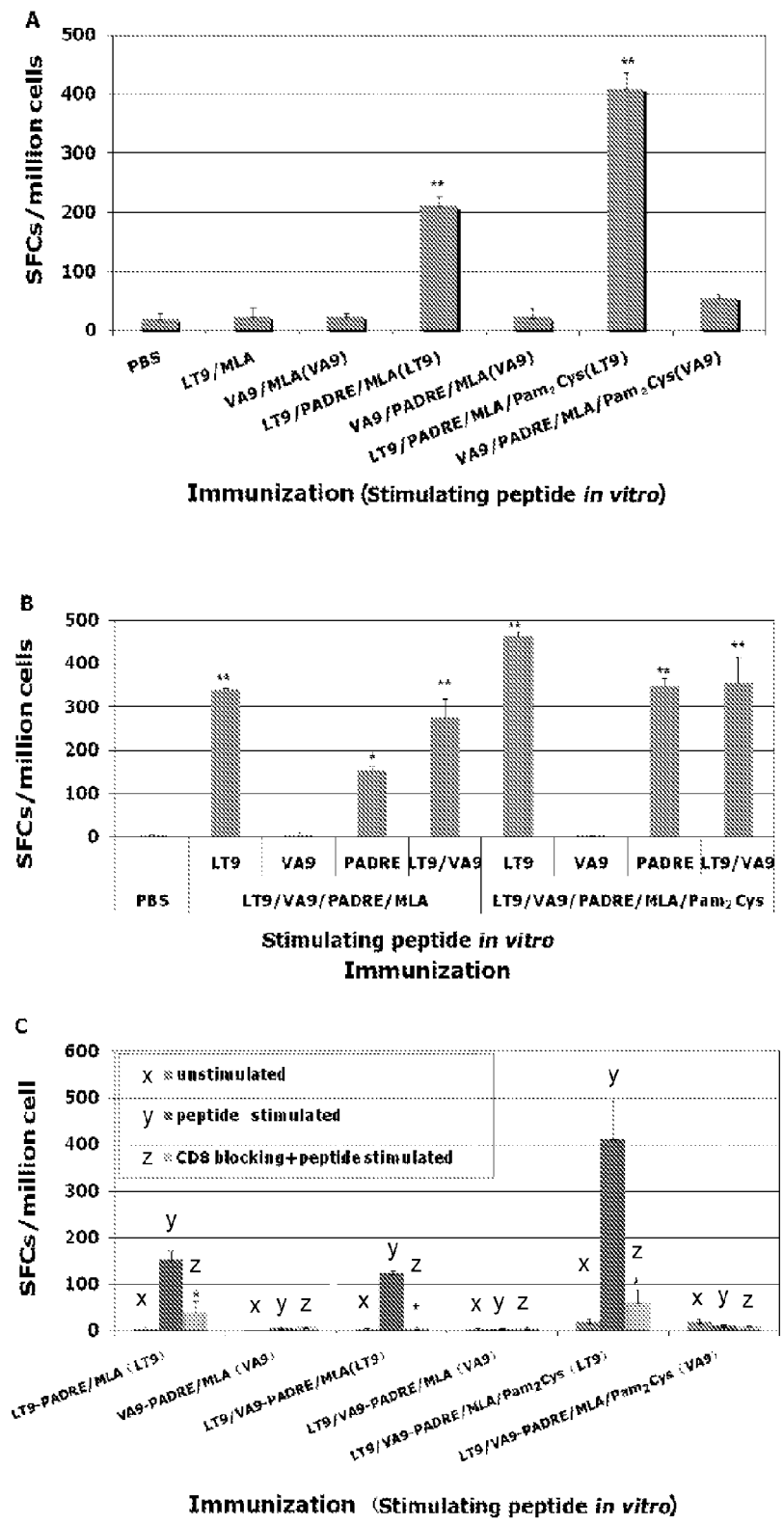
FIG. 4. Immunogenicity of LT9 and VP9 in HLA transgenic mice. (A) HLA-B*0702-transgenic mice immunized with PBS as a control, peptides (LT9: LPQFATAAT (SEQ ID NO: 8); VA9: VPFVVFLVA (SEQ ID NO: 9)) prepared as follows: peptide alone, peptide plus PADRE, peptide plus PADRE and Pam₂Cys, all these immunogens mixed with MLA. Immunization was given three times at two week intervals. Ten to fourteen days after the last immunization, spleen cells were obtained from immunized mice and stimulated by the specified peptide in an ex vivo IFN-γ ELISPOT assay. (B) HLA-B*0702 mice immunized with peptide pools and tested for recall responses with LT9 or VA9 or PADRE. HLA-B*0702 transgenic mice immunized with mixtures of two identified peptides (LT9 and VA9), PADRE or Pam₂Cys mixed with MLA, three times at two week intervals. Fourteen days after the last immunization, spleens were removed from immunized mice and splenocytes were cultured with peptides, LT9 or VA9 or PADRE. The results are expressed as IFN-γ spot formation by one million cells. Data presented are a representative example from three independent experiments. (C) IFN-γ spot formation was significantly reduced in the presence of anti-CD8 antibody. Splenocytes from immunized mice were incubated with antibodies to CD8, and their isotype control for 60-90 min prior to stimulation with LT9 or VA9. *, $P<0.05$; **, $P<0.01$. IFN-γ spot formation was tested for splenocytes from mice that received different vaccine formulations in the absence or presence of blocking antibody.
Figure 5A:
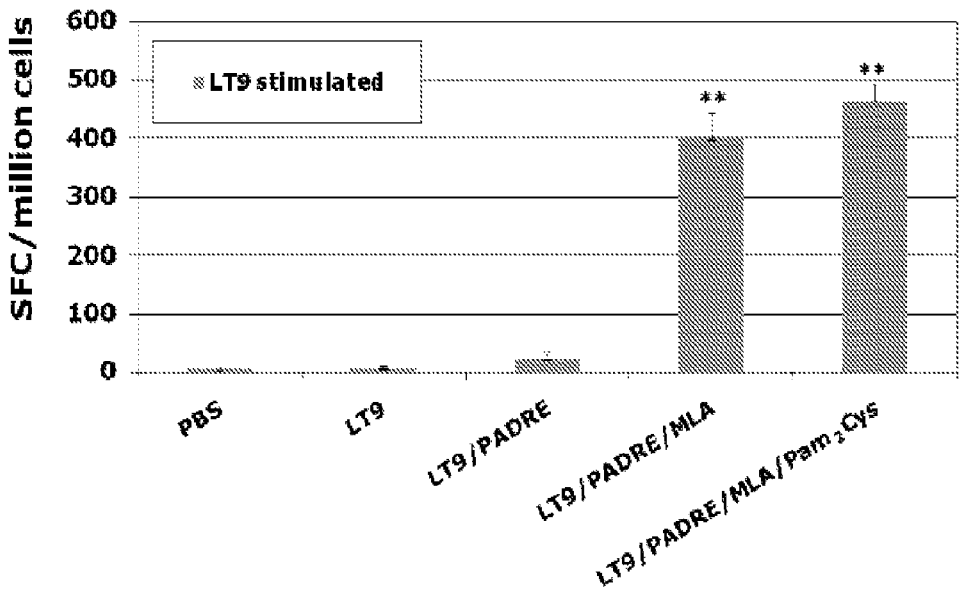
FIG. 5. LT9-specific response induced by LT9 immunization. Mice were immunized with LT9 peptide alone, LT9/PADRE, LT9/PADREMLA/Pam₂Cys. IFN-γ production (A) and lymphocyte proliferation (B) were tested 2 weeks after last immunization. *, $P<0.05$; **, $P<0.01$ FIG. 6. PADRE-specific T cell responses were evaluated in immunized group. (A,B) PADRE-specific IFN-γ spot formation and spleen cell proliferation were tested by splenocytes from LT9 formulation immunized B7 mice exposed to PADRE peptide. *, $P<0.05$; **, $P<0.01$. (C) Blocking CD4⁺ T cell receptor using anti-CD4⁺ Ab significant decreases IFN-γ production in the following group.
Figure 5B:
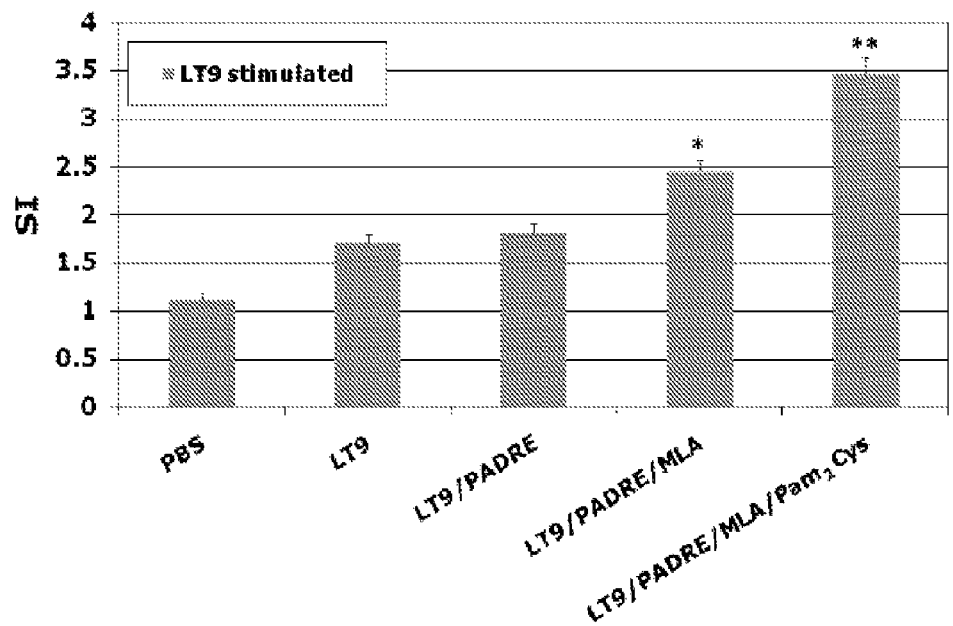
Figure 6:
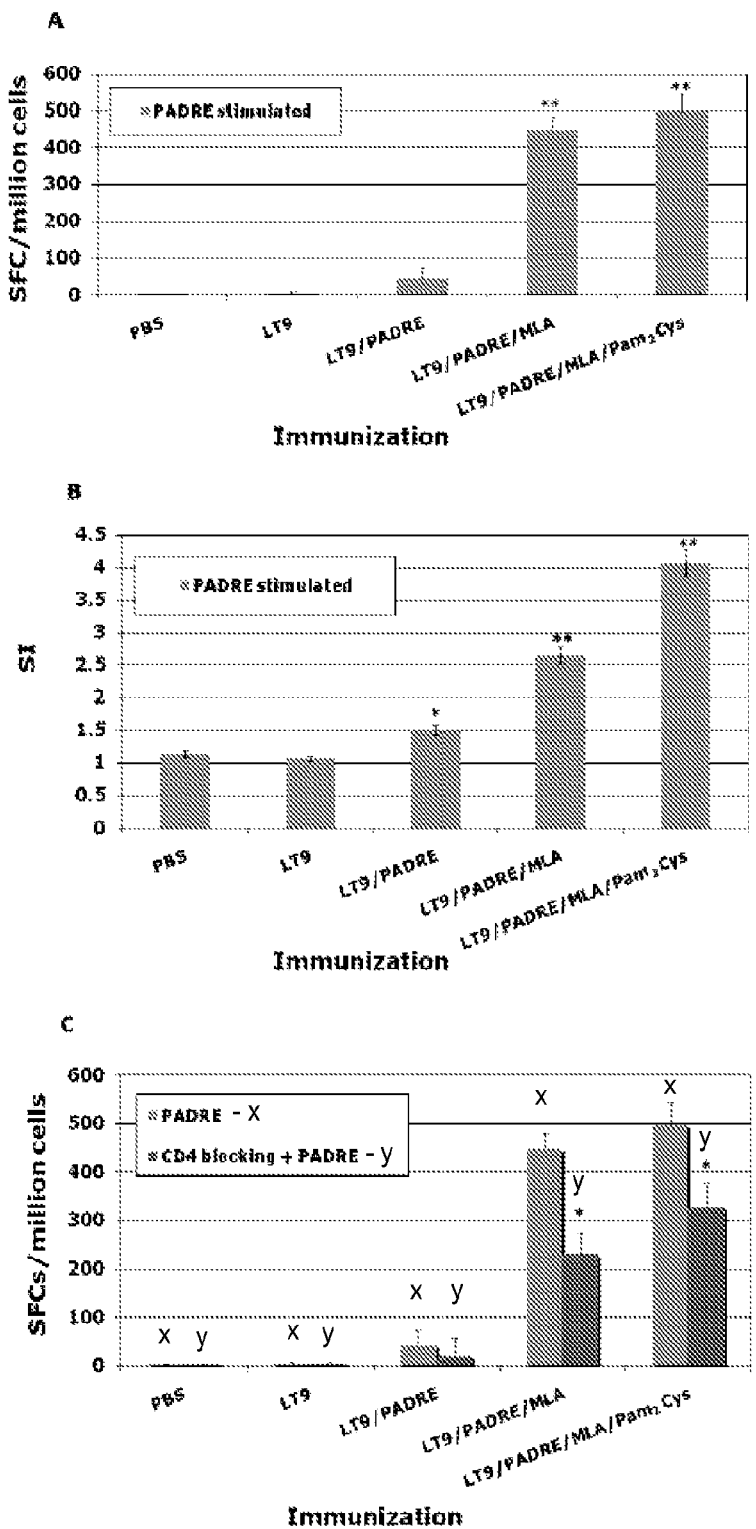
Figure 7:
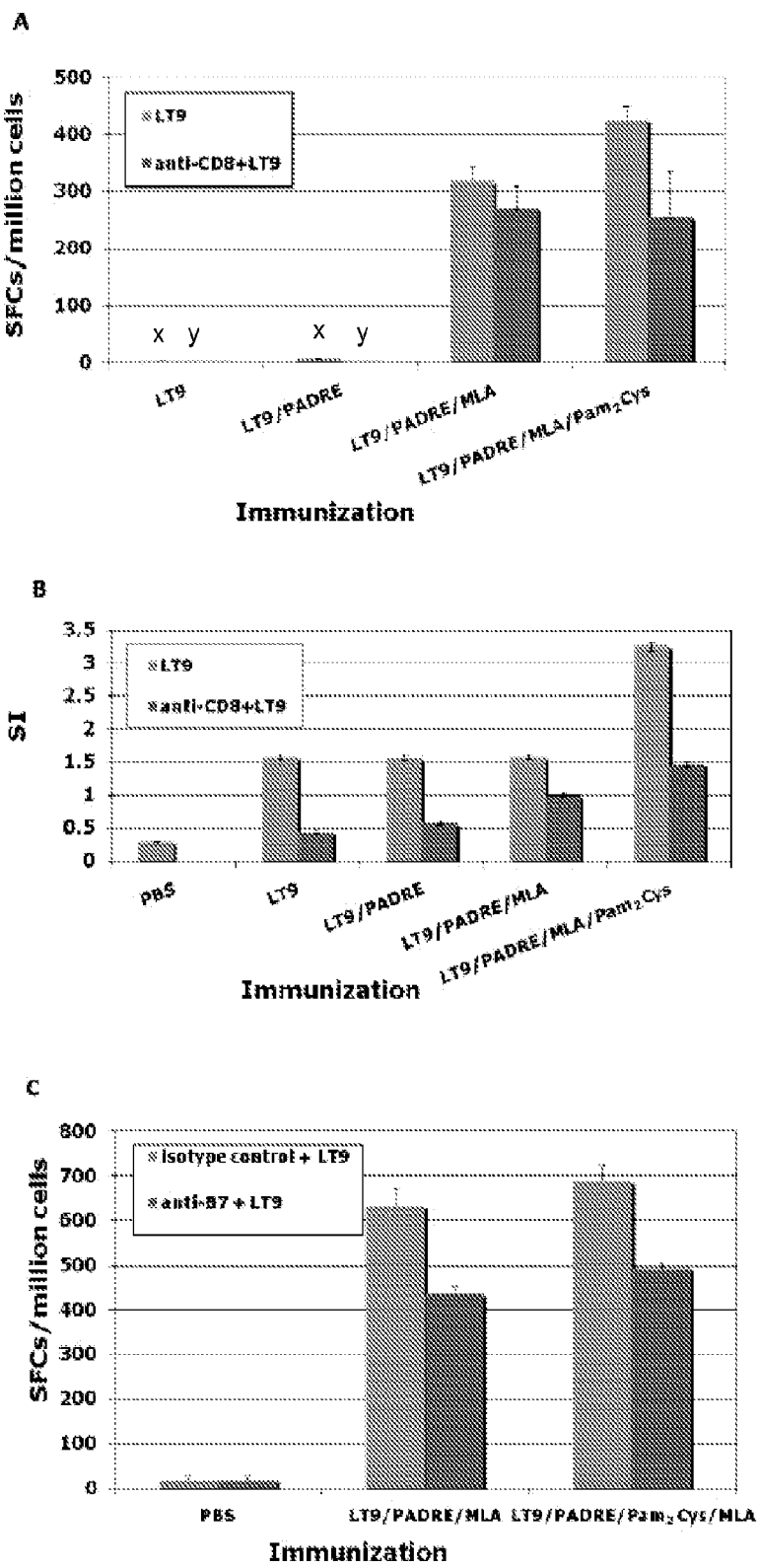
FIG. 7. LT9 peptides with adjuvants induce HLA-B07-restricted CD8⁺ T cell responses in immunized mice. LT9-specific IFN-γ response and lymphocyte proliferation were measured by blocking CD8 (A,B) and HLA-B07®. In each immunization, the control is the left-hand bar. Splenocytes were isolated from peptide-immunized HLA-B07 transgenic mice 10 days after immunization and incubated with antibodies to CD8α or HLA-B07 and their common isotype control for 60-90 min prior to stimulation with LT9. Their abilities to generate IFN-γ and lymphocyte proliferation in response to peptide were tested. *, $P<0.05$; **, $P<0.01$.
Figure 8:
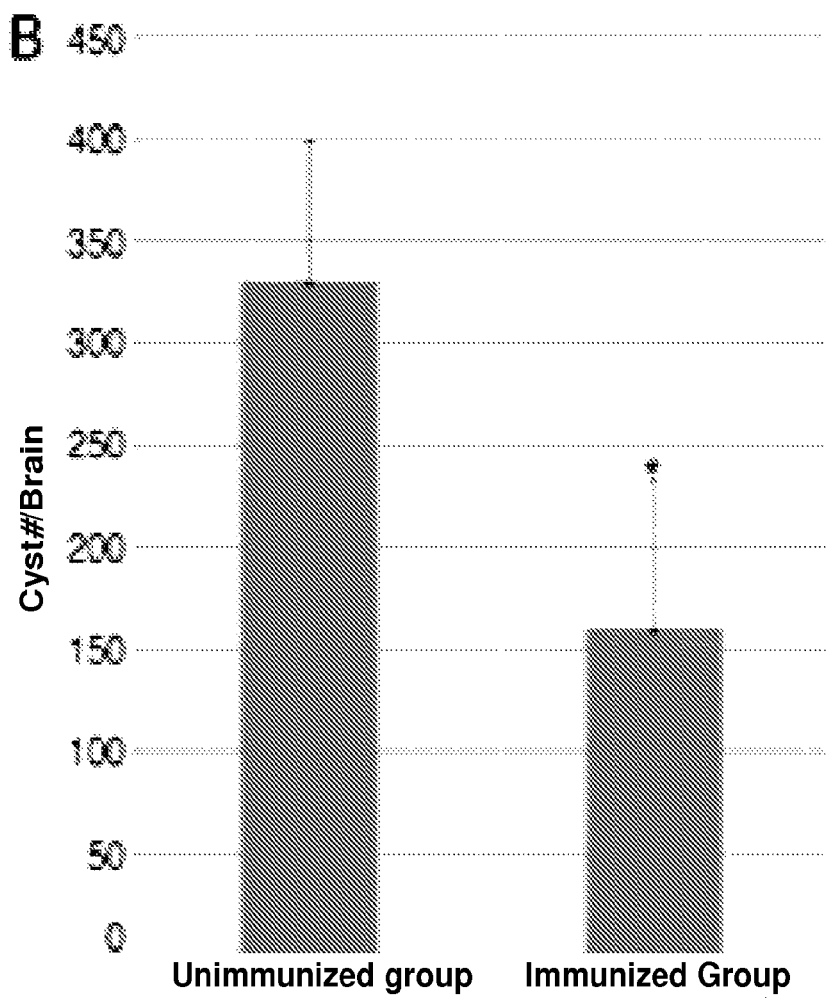
FIG. 8. Replication of *T. gondii* luciferase expressing parasites were significant reduced in HLA-B07 mice immunized with LT9/PADRE/MLA/Pam₂Cys assayed from 6 days after challenge and cyst formation in day 30. HLA-B07 transgenic mice were either not immunized or immunized with LT9/PADRE/MLA/Pam₂Cys three times 14 days apart. Two weeks after vaccine administration, transgenic mice were challenged with 10,000 Pro(Fluc)-type II *T. gondii* luciferase expressing parasites. Average cyst enumeration was performed in the brains of mice challenged 30 days after final immunization. The data represent the means. There were a total of 5-9 mice tested in each control or immunization group. Asterisks indicate significant differences compared to the control.

Because the three linked peptides in the lipopeptide formulation were not effective and a mixture of the components with a single peptide was as robust or more robust than the lipopeptide, the approach with the three peptides that had been included in the linked lipopeptide with the universal helper CD4$^+$ T cell peptide, PADRE, and adjuvants was tried as described below. The response was robust both in vivo (FIG. 3) and in vitro.

Mice immunized with mixture of CD8$^+$ and CD4$^+$ epitope peptides and lipid Pam$_2$Cys emulsified in MLA elicited higher IFN-γ production than mice immunized with lipopeptides constructed with the same components of CD4$^+$, CD8$^+$, and Pam$_2$Cys. The approach using cocktails of non-covalently linked lipid mixed to HTL and CTL epitopes for simultaneous induction of multiple CTL specificities is preferred for some vaccine embodiments.

HTL responses are preferred for the development of CTL responses, at least in the case of lapidated covalently or non-covalently linked HTL-CTL epitope constructs formulated in PBS. Several previous studies have illustrated a role for CD4$^+$ responses for development of CD8 CTL responses, both in human and in experimental animals. The inclusion of PADRE, a synthetic peptide that binds promiscuously to variants of the human MHC class II molecule DR and is effective in mice, also augmented CD8$^+$ T cell effector functions by inducing CD4$^+$ T helper cells. Both CD4$^+$ and CD8$^+$ epitopes were targeted in order to drive a protective immune response.

Adjuvanting antigens contributes to the success of vaccination. An example herein is that 3-deacylated monophosphoryl lipid A (MLA), a detoxified derivative of the lipopolysaccharide (LPS) from *Salmonella minesota* R595 was a potent adjuvant. This is a Toll-like receptor 4 (TLR4) agonist and thus a potent activator of Th1 responses. It has been used as an adjuvant in human vaccine trials for several infectious disease and malignancy indications. It has been very effective as an adjuvant providing CD4$^+$ T cell help for immunizations against other protozoan infections such as leishmaniasis. A robust response was observed when MLA was included in preparation for immunization of mice. Pam$_2$Cys (S-[2,3-bis(palmitoyloxy)propyl]cysteine) is a lipid component of macrophage-activating lipopeptide. Pam$_2$Cys binds to and activates dendritic cells by engagement of Toll-like receptor 2 (TLR-2). Toll-like receptors (TLRs) function as pattern-recognition receptors in mammals. It is suggested that both TLR2 and TLR4 receptors might participate in the host defense against *T. gondii* infection through their activation by the GPIs and could work together with other MyD88-dependent receptors, like other TLRs, to elicit an effective host response against *T. gondii* infection. In our study, there was a slightly more robust response observed when Pam$_2$Cys was co-administered for some peptide.

HLA-restricted epitopes from *Toxoplasma gondii* have been evaluated and shown to provide protection against parasite challenge. Various peptide-based approaches to induction of IFN-γ responses were evaluated as part of ongoing efforts to develop immunosense vaccines for use in humans. Robust protection was achieved in the HLA-A*1101 transgenic mice challenged with type II parasites following immunizations. In order to identify additional peptides from *T. gondii* that were present in tachyzoites or bradyzoites or sporozoites of Type I and II strains and elicited IFN-γ from HLA-A03$^+$ supertype (which includes the HLA*1011 alelle) restricted CD8$^+$ T cells, bioinformatic algorithms were utilized to identify novel, *T. gondii*-derived, epitopes restricted by the HLA-A03 supertype. Then PBMC cells were tested to determine whether the peptides elicited IFN-γ from human CD8$^+$ T cells from seropositive persons. This was intended to collectively provide broad coverage for the human population with HLA-A03 supertype worldwide. The additional peptides identified as immunogenic for human peripheral blood cells were also robust in eliciting IFN-γ and when used to immunize mice.

III. Cellular Immunogenicity of Two Identified B7 Restricted CD8+ T Cell Epitope Peptides in HLA B*0702 Transgenic Mice.

To address the capacity of two identified B7 epitopes, $GRA7_{20-28}$ (LPQFATAAT (SEQ ID NO: 8)) and $GRA3_{27-35}$ (VPFVVFLVA (SEQ ID NO: 9)), to prime for IFN-γ responses, HLA-B07 transgenic mice were immunized s.c. with each of peptides alone and peptides with PADRE or peptides with PADRE and $Pam_2Cys$. Each of these regents was mixed with MLA. A mixture of these two peptides with PADRE, or plus $Pam_2Cys$ mixed with MLA were also used as immunogens. Little IFN-γ responses were observed following immunization by peptides mixed with MLA alone. When PADRE was added for immunization, a significant amount of IFN-γ was produced following stimulation by one B7 epitope peptide LT9 (LPQFATAAT (SEQ ID NO: 8)) in vitro (P=0.0003, compared to peptide mixed with MLA alone). An even more robust response was achieved when $Pam_2Cys$ was added to the immunogen. In contrast, no significant amount of IFN-γ was produced using splenocyte groups immunized with another B7 epitope peptide VA9 (VPFVVFLVA (SEQ ID NO: 9)) (P>0.05, compared to control group), when they were stimulated by this peptide.

Similar results were found with peptide pool immunizations. Splenocytes from the mice immunized with the mixtures of two peptides LT9 and VA9 with PADRE or plus $Pam_2Cys$ mixed with MLA produced significant amount of IFN-γ when stimulated by LT9 (P<0.001, compared to the PBS immunization group), but not by VA9 (P>0.05, compared to the PBS immunization group).

To assess relative contributions of CD8+ T cells to overall IFN-γ response, the activity of splenic CD8+ T cells was blocked using antibody specific to the CD8+ T cell receptor. IFN-γ spot formation was significantly reduced in the presence of αCD8 incubated with the spleen cells from mice immunized with LT9 included in the vaccination and stimulated by LT9.

Relation Between Solubility and Immunogenicity

The correlation between the solubility of the peptides and their immunogenicity is summarized in Table 4. The VA9 was much less soluble with overall percent solubility of 10%. In contrast, LT9 had 99% solubility. LT9 was effective in the peptide vaccine construct, but VA9 was not. Reduced solubility of this peptide in the vaccine correlated with its reduced immunogenicity.

Evaluation of Cellular Immune Responses to LT9 Formulated Peptide Vaccine

Since VA9 peptide formulation vaccination of HLA-B*0702 transgenic mice could not effectively elicit CD8+ T cell to produce IFN-γ, only LT9 peptide formulations were evaluated for protection in HLA-B07 transgenic mice in subsequent studies.

The ability of MLA and $Pam_2Cys$ to adjuvant the LT9 peptide also was evaluated. Mice were immunized with LT9 peptide alone, LT9/PADRE, LT9/PADRE/MLA, LT9/PADRE/MLA/$Pam_2Cys$. Immunization with LT9 alone did not induce effective IFN-γ production, but when the PADRE helper epitope was included in the immunogens, it induced a small amount of IFN-γ but this was not significant (P=0.057, when compared to peptide alone). When MLA was added, robust CD8+ T cell production of IFN-γ was achieved (P=0.0001, compared to peptide alone; P=0.00013 compared to peptide/PADRE). Greater responses were observed when $Pam_2Cys$ was added in the vaccine (P=0.000009, compared to peptide alone; P=0.000013, compared to peptide/PADRE; P=0.09, compared to peptide/PADRE/MLA). However, the addition of $Pam_2Cys$ to PADRE/MLA did not significantly enhance the LTP specific IFN-γ response. Thus, MLA is an effective adjuvant to enhance IFN-γ production in response to CD8+ T cell eliciting peptides in HLA-B*0702 transgenic mice.

LT9-specific proliferative responses with a SI of ~3.5 were observed following immunization with LT9/PADRE/MLA/$Pam_2Cys$. When the same peptide epitope was used alone for immunization, SI was 1.5. The magnitude of lymphocyte blastogenesis and IFN-γ elicited by LT9 with adjuvants had the same patterns.

PADRE Delivers Help for Peptide-Specific CTL Response

In order to determine function of the CD4+ T cell epitope PADRE in this peptide vaccine, PADRE-specific T cell responses were evaluated by IFN-γ ELISPOT assay and a proliferative response assay using splenocytes from the immunized mice. Immunization with the CD8+ T cell epitope alone did not induce an IFN-γ response, whereas when the CD4+ T cell epitope PADRE was added to the immunogen, CD8+ T cells could be activated to secrete IFN-γ (P=0.0006 compared to PBS group; P=0.001 compared to peptide alone immunized group). A proliferative response of SI~4, was observed following immunization with LT9 plus PADRE and $Pam_2Cys$ in MLA. However, blocking the CD4+ T cell receptor using anti-CD4+ antibody significantly reduced IFN-γ production, thus indicating that PADRE is an effective CD4+ Th epitope which contributes to the peptide vaccine construct. However, in some instances, PADRE elicited only a small enhancement of the response to LT9.

LT9 Peptide Elicited HLAB7-Restricted CD8+ T Cells Responses in Immunized Mice.

Splenocytes were isolated from peptide-immunized HLA-B07 transgenic mice 10 days after immunization and incubated with antibodies to αCD8 or HLA-B07 and their common isotype control prior to stimulation with LT9. Their abilities to generate IFN-γ and lymphocyte proliferation in response to peptide were tested. To study the ability of αHLA-B*0702 to block response of CD8+ T cells in the same experiment, blocking αCD8 T cells and blocking αHLA-B*0702 were used with the same spleen cells in the same experiment. The data shows that blocking CD8+ T cell receptors using αCD8+ antibody significantly reduced LT9-specific IFN-γ production and T cell proliferation (P<0.05).

Then, to further analyze the association of LT9 presentation by HLA-B*0702, blocking experiments using a monoclonal anti-HLA-B*0702 antibody (BB7.2) was performed. Results indicated that the IFN-γ secretion was significantly decreased by the anti-HLA-B07 antibody but not by the control antibody (p<0.05). These results demonstrate that the peptide specific IFN-γ response is HLA-B*0702 restricted and involves CD8+ T cells. The partial blocking by the HLA B7 antibody is likely a function of the antibody's capacity for blocking, and not reactivity of the peptide with the murine H2 haplotypes. This is because the algorhithms predict poor affinity of all of the background Balb/c and B6 H2 molecules with these peptides. Using the IEDB to predict, these peptides are predicted to bind poorly to these H-2 molecules.

Peptide with Adjuvant Vaccination Protects Mice Against Type II Parasite Challenge HLA-B*0702 transgenic mice were immunized with the LT9 peptide plus PADRE and $Pam_2Cys$ in MLA three times at two week intervals. Mice were challenged 2 weeks after the last immunization. They were imaged 5 days post-challenge with 10,000 Pru (Fluc) using the Xenogen in vivo imaging system. The numbers of luciferase expressing parasites in immunized HLA-B*0702 mice were significantly reduced compared to the numbers of parasites in unimmunized mice. There was also a significant reduction of cysts in the brain when mice were immunized with LT9 peptide vaccine. There was a 54% reduction from a mean of 335 to 155 cysts per brain.

Discussion

Herein, two *T. gondii*-specific HLA-B*07 restricted CD8+ T cell epitopes LT9 (LPQFATAAT (SEQ ID NO: 8)) and VA9 (VPFVVFLVA (SEQ ID NO: 9)) derived from GRA7$_{20-28}$ and GRA3$_{27-35}$ elicited IFN-γ from human PBMC cell, 4 HLA-B07 seropositive and 0 of 3 seronegative persons. Upon immunization of mice, only LPQFATAAT (SEQ ID NO: 8) elicited CD8+ T cell specific IFN-γ with the help of a universal CD4+ epitope and adjuvants, MLA and Pam$_2$Cys, enhanced the response. This peptide vaccine plus adjuvants protect HLA-B07 transgenic mice from type II parasite challenge.

CD8+ T cell epitopes identified were from dense granule (GRA) proteins of *Toxoplasma gondii*. Many studies have shown that dense granule antigens (GRA) are involved in parasite survival and virulence (Mercier C, et al. (2005). The proteins are secreted in abundance and circulate in the blood stream during the first hours following infection and appeared 2-5 days after mice infected with parasite. The GRA proteins have thus been considered to be attractive vaccine candidates for the prevention and control of toxoplasmosis.

Two peptides were recognized by T cells from *T. gondii* specific HLA-B07 restricted PBMC. However, although peptide VPFVVFLVA (SEQ ID NO: 9) was recognized by T cells from *Toxoplasma gondii*-specific HLA-B07-restricted human PBMC, it did not induce a significant IFN-γ response in HLA-B*0702 transgenic mice. We therefore concluded that VA9 was presented by HLA-B07 supertype molecules to CD8+ T cells in humans, but was not present in significant quantity to be presented by HLA-B07 supertype molecules to CD8+ T cells in the transgenic mice. This seems most likely to be due to the relative insolubility of the VA9 peptide. The VA9 peptide was 90% insoluble with overall percent solubilities of 10% in PBS. In contrast, LT9 was soluble, with 99% solubility in PBS. LT9 was effective in the peptide vaccine construct, but VA9 was not, reduce solubility of peptides in the vaccine peptides might correlate with reduced immunogenicity.

The inclusion of PADRE, a synthetic nonnatural Pan HLA DR binding Epitope peptide that binds promiscuously to variants of the human MHC Class II molecule DR and is effective in human and HLA transgenic mice, can augment CD8+ T cell effector functions by inducing CD4+ T helper cells. The PADRE epitope was demonstrated to deliver help for a MHC Class I restricted peptide-specific CTL response to the *T. gondii* peptide herein. Preference for CD4+ T cell help in the generation of a CD8+ T cell response also has been proved in viral, bacterial, and parasite models. In studies of *Trypanosoma cruzi* infections (Padilla A, et al. 2007), it was demonstrated that CD4+ T cell help is required during the primary response to immunodominant epitopes. In a vaccine, both CD4+ and CD8+ epitopes should be targeted in order to drive a protective immune response.

Although peptide vaccines including CD4+ and CD8+ epitopes could prime cell-mediated immune responses, low-molecular-weight synthetic peptide antigens are not highly immunogenic by themselves. These observations have led to investigations to co-administer adjuvants with vaccine antigens to potentiate activity of vaccines and the weak immunogenicity of the synthetic epitopes. Adjuvanting antigens contribute to the success of vaccination 3-deacylated monophosphoryl lipid A (MLA) a detoxified derivative of the lipopolysaccharide (LPS) from *Salmonella minesota* R595 which is a Toll-like receptor 4 (TLR4) agonist and thus a potent activator of Th1 responses. It has been used as an adjuvant in human vaccine trials for several infectious diseases and cancer. It has been very effective as an adjuvant providing CD4+ T cell help for immunizations against other protozoan infections such as leishmaniasis. In our study, a robust response was observed when MLA was included in preparation for immunization of mice. Pam$_2$Cys (S-[2,3-bis (palmitoyloxy)propyl]cysteine) is a lipid component of macrophage-activating lipopeptide. Pam$_2$Cys binds to and activates dendritic cells by engagement of Toll-like receptor 2 (TLR-2). Toll-like receptors (TLRs) function as pattern-recognition receptors in mammals. It is suggested that both TLR2 and TLR4 receptors might participate in the host defense against *T. gondii* infection through their activation by the GPIs and could work together with other MyD88-dependent receptors, like other TLRs, to obtain an effective host response against *T. gondii* infection. In our study, an even more robust response was observed in the Pam$_2$Cys co-administration group and robust protection was achieved in the transgenic mice challenged with type II parasites following immunizations.

The work presented herein indicates that an HLA-B07 restricted epitope LT9 (LPQFATAAT (SEQ ID NO: 8)) derived from GRA7$_{20-28}$ that can elicit IFN-γ from T cells of seropositive HLA-B07 persons elicits IFN-γ and CD8+ T cells when administered with a universal DR epitope PADRE for CD4+ help and MLA and Pam$_2$Cys to adjuvant MHC Class I-restricted CD8+ T cells. This peptide vaccine reduced parasite burden in immunized mice challenged with type II parasites. This is the first report of a *T. gondii* specific HLA-B07 restricted CD8+ T cell epitope based vaccine that protects HLA-B07 transgenic mice against *T. gondii*.

Materials and Methods

I. Bioinformatic prediction of CD8+ T cell epitopes ARB, SMM, and ANN algorithms from the immunoepitope database (IEDB) http://www.iedb.org/ were used to predict binding affinity to HLA-A*0201 of *T. gondii* specific peptides. Protein sequences from GRA10, GRA15, SAG2C, SAG2D, SAG2X, SAG3, SRS9, BSR4, SPA, and MIC were screened for nonamer or decamer CD8+ T cell epitopes based on their predicted binding affinity to HLA-A*02 supertype molecules. A total of 29 unique peptides that had IC$_{50}$<50 nM using the bioinformatic algorithm were selected. Protein sequences were from ToxoDB 5.1. Population coverages of peptides were predicted as described in Bui H H, et al. (2007).

Peptides and GLA-SE

All peptides were synthesized by Synthetic Biomolecules (San Diego, Calif.) and were >90% pure. Peptides were first dissolved in DMSO and then diluted in PBS or media. GLA-SE mimetic was synthesized by Infectious Diseases Research Institute (IDRI, Seattle, Wash.).

MLA=GLA-SE

MHC-Peptide Binding Assays

Quantitative assays to measure binding of peptides to HLA Class I molecules are based on inhibition of binding of a radiolabeled standard peptide. Assays were performed as described in Cheng Y and Prusoff W H (1973) and Gulukota, K., et al. (1997). Briefly, 1-10 nM of radiolabeled peptides were co-incubated with 1 M-1 nM purified MHC and 1-3 human β$_2$-microglobulin. After 2 days, binding of radiolabeled peptide to corresponding MHC Class I molecule was determined by capturing MHC-peptide complexes on Greiner GREINER® Lumitrac 600 microplates coated with W6/32 antibody and measuring bound counts per minutes using a Topcount microscintillation counter. Concentration of peptide yielding 50% inhibition of binding of radiolabeled probe peptide (IC$_{50}$) then was calculated. Under conditions used, where [radiolabeled probe]<[MHC] and $IC_{50} \geq$[MHC], measured $IC_{50}$ values are reasonable approximations of true $K_d$ values.

Mice

HLA-A*0201 $K_d$ transgenic mice were produced at Pharmexa-Epimmune (San Diego, Calif.) and bred at the University of Chicago. All studies were conducted with Institutional Animal Care and Use Committee at the University of Chicago approval.

Enzyme-Linked Immunospot (ELISpot) Assay

Cryopreserved peripheral blood mononuclear cells (PBMC), obtained in accordance with institutional and NIH guidelines, from both *T. gondii*-seropositive and seronegative individuals were used in ELISpot assays to study human PBMCs. PBMCs were isolated from heparinized blood samples by density gradient centrifugation using Histopaque (Sigma-Aldrich), then washed twice with PBS, and cryopreserved in AIM-V medium (Gibco) containing 20% FCS and 10% DMSO.

$2 \times 10^5$ PBMCs per well were incubated at 37° C., 5% $CO_2$ in AIM-V medium, pulsed by peptide or peptide pools at 10 µg/ml in MSIPS4W10 Multiscreen HTS-IP 96-well plates (Millipore, Bedford, Mass.) previously coated with 50 µl of 15 µg/ml anti-human IFN-γ (1-D1K) monoclonal antibody (mAb) in sterile PBS overnight, and then processed as described in Tan T G et al. (2010). After washing with sterile PBS and blocking with RPMI-1640 medium containing 10% FCS at room temperature for 2-3 hr, plates were successively incubated with 100 µl of 1 ng/ml biotinylated anti-human IFN-γ mAb (7B6-1) for 2 hr and streptavidin-conjugated alkaline phosphatase at a 1:1000 dilution for 1 hr at room temperature. Wells were washed with PBS between incubation stages. Spots were developed using 5-bromo-4-chloro-3-indolyl-phosphate/p-nitro blue tetrazolium chloride (BCIP/NBT) and quenched by extensive washing with distilled water. After drying, plates were counted using an automated ELISpot reader (CTL ImmunoSpot). Media containing an equivalent concentration of DMSO was used to measure background response levels, and 5 µg/ml of *T. gondii* ysates antigen (TLA) was used as a positive control.

ELISpot assays for production of IFN-γ by murine splenocytes were performed similarly, except that anti-mouse IFN-γ mAb (AN18) and biotinylated α-mouse IFN-γ mAb (R4-6A2) were used as cytokine-specific capture and detection antibodies instead. $5 \times 10^5$ splenocytes were plated per well. All antibodies and reagents used for ELISpot assays were obtained from Mabtech (Cincinnati, Ohio). Cells were plated in at least 3 replicate wells for each condition. Results were expressed as number of spot forming cells (SFCs) per $10^6$ PBMCs or per $10^6$ murine splenocytes.

Immunizations and Challenge

Age-matched female HLA-A*0201 mice were inoculated subcutaneously (s.c.) at the base of the tail using a 30-gauge needle with pooled CD8+ T cell peptides as shown in Table 1, with pan DR epitope (PADRE), a universal helper T lymphocyte epitope emulsified in 3-deacylated monophosphoryl lipid A (GLA-SE). Controls were injected with PBS. Mice were boosted once at a 2-week interval. Mice were challenged intraperitoneally with 10,000 Pru-FLUC tachyzoites 10-14 days after the last immunization.

Ex Vivo Preparation of Murine Splenocytes

Three to five mice from each group were euthanized 7 to 14 days after the last immunization. Spleens were harvested, pressed through a 70 µm screen to form a single-cell suspension, and depleted of erythrocytes with ASK lysis buffer (160 mM $NH_4Cl$, 10 mM $KHCO_3$, 100 µM EDTA). Remaining splenocytes were washed twice with Hank's Balanced Salt Solution (HBSS) and resuspended in complete RPMI medium (RPMI-1640 supplemented with 2 mM L-GlutaMax [Invitrogen], 100 U/ml penicillin, 100 µg/ml streptomycin, 1 mM sodium pyruvate, 50 M β-mercaptoethanol, and 10% FCS) before use in subsequent in vitro assays.

In Vivo Bioluminescence Imaging

Mice infected with Pru-FLUC tachyzoites were imaged at day 7 post-challenge using the in vivo imaging system (IVIS; Xenogen, Alameda, Calif.) Mice were injected i.p. with 200 µl of D-luciferin and immediately anesthetized in an $O_2$-rich induction chamber with 2% isoflurane. After 12 min, mice were imaged in ventral positions and photonic emissions were assessed using Living Image® 2.20.1 software (Xenogen). Data were presented as pseudocolor representations of light intensity and mean photons/s/region of interest (ROI).

Statistical Analyses

Statistical analyses for all in vitro assays were performed using a 2-tailed student's T test. Peptides were considered immunogenic in mice if they induced IFN-γ spot formation from immunized mice that was significant (P<0.05) relative to spot formation from control mice. Peptides and peptide pools were considered immunogenic in humans if they induced IFN-γ spot formation from PBMCs that was significant (P<0.05) relative to spot formation from the same cells incubated with media containing an equivalent concentration of DMSO. Each ELISpot experiment was replicated a minimum of twice. P values of ≤0.05 were considered significant.

Single letter designations are used for amino acids throughout.

II. Peptides and Lipopeptides

HLA-A03 supertype CD8+ T cell epitopes included: KSFKDILPK ($SAG1_{224-232}$) (SEQ ID NO: 4), AMLTAFFLR ($GRA6_{164-172}$) (SEQ ID NO: 5), and RSFKDLLKK ($GRA7_{134-142}$) (SEQ ID NO: 6). PADRE (AKFVAAWTL-KAAA (SEQ ID NO: 7)) was the universal CD4 helper peptide used in vaccine constructs. $Pam_2Cys$ ($Pam_2$-KSS) also was included. Peptides and lipopeptides were synthesized by Synthetic Biomolecules, San Diego at >90% purity. Additional HLA-A03 supertype bound peptides and their initial grouping into pools for in vitro studies are shown in Tables 2 and 3. A TLR4 agonist, a MLA mimetic, was synthesized by the Infectious Diseases Research Institute (Seattle, Wash.) as a stable oil-in-water emulsion. AMLTAFFLR ($GRA6_{164-172}$) (SEQ ID NO: 5) and additional new peptides were first dissolved in DMSO and then diluted in PBS.

Mice

HLA-A*1101/$K^b$ transgenic mice were produced at Pharmexa-Epimmune (San Diego, Calif.) and bred at the University of Chicago. These HLA-A*1101/$K^b$ transgenic mice express a chimeric gene consisting of the 1 and 2 domains of HLA-A*1101 and the 3 domain of H-2$K^b$, and were created on a C57BL/6 background. All studies were conducted with approval of the Institutional Animal Care and Use Committee at the University of Chicago.

Parasites

Transgenic *T. gondii* used for in vivo challenges was derived from type II Prugniaud (Pru) strain and expresses the firefly luciferase (FLUC) gene constitutively by tachyzoites and bradyzoites. It was created, maintained and utilized as previously described in Saeij, et al. (2005) and Kim, S. K. et al. (2007).

Immunizations and Challenge

To evaluate peptide immunogenicity, HLA-A*1101 transgenic mice were inoculated subcutaneously (s.c.) at the base of the tail using a 30-gauge needle with single peptides or a mixture of CD8+ T cell peptides (50 µg of each peptide per mouse) and PADRE (AKFVAAWTLKAAA (SEQ ID NO:

7)) emulsified in 20 μg of MLA (TLR4 agonist) with or without Pam₂Cys. For immunization with lipopeptides, HLA-A*1101 mice received 20 nmol lipopeptide dissolved in PBS and emulsified in MLA. As controls, mice were injected with PBS. Mice were vaccinated twice at 3-week intervals. For challenge studies, mice were immunized with peptide emulsions and challenged intraperitoneally (i.p.) 14 days post-immunization using Type II parasites.

In Vivo Bioluminescence Imaging

Mice infected with 20,000 Pru-FLUC tachyzoites were imaged 7 days post-challenge using the in vivo imaging system (IVIS; Xenogen, Alameda, Calif.). Mice were injected i.p. with 200 μl of D-luciferin, anesthetized in an $O_2$-rich induction chamber with 2% isoflurane, and imaged after 12 minutes. Photonic emissions were assessed using Living Image® 2.20.1 software (Xenogen). Data are presented as pseudocolor representations of light intensity and mean photons/s/region of interest (ROI).

ELISpot Assay

Murine splenocytes: Mice were euthanized 7 to 14 days after immunization. Spleens were harvested, pressed through a 70 μm screen to form a single-cell suspension, and depleted of erythrocytes with AKC lysis buffer (160 mM $NH_4Cl$, 10 mM $KHCO_3$, 100 μM EDTA). Splenocytes were washed twice with Hank's Balanced Salt Solution (HBSS) and resuspended in complete RPMI medium (RPMI-1640 supplemented with 2 mM L-GLUTAMAX [Invitrogen], 100 U/ml penicillin, 100 μg/ml streptomycin, 1 mM sodium pyruvate, 50 μM β-mercaptoethanol, and 10% FCS) before they were used in subsequent in vitro assays.

ELISpot assays with murine splenocytes were performed using α-mouse IFN-γ mAb (AN18) and biotinylated α-mouse IFN-γ mAb (R4-6A2) as the cytokine-specific capture antibodies. $5 \times 10^5$ splenocytes were plated per well.

Human PBMC: PBMC were obtained, HLA haplotyped, processed and cryopreserved as described in Tan, T. G. (2010). ELISpot assays with human PBMCs were similar to those with murine splenocytes but used α-human IFN-γ mAb (1-D1K) with biotinylated α-human IFN-γ mAb (7B6-1) with $2 \times 10^5$ PBMCs per well. All antibodies and reagents used for ELISpot assays were from Mabtech (Cincinnati, Ohio).

Both murine and human cells were plated in at least 3 replicate wells for each condition. Results were expressed as number of spot forming cells (SFCs) per $10^6$ PBMCs or per $10^6$ murine splenocytes.

Bioinformatic Predictions and MHC-Peptide Binding Assays

Protein sequences derived from GRA10, GRA15, SAG2C, SAG2D, SAG2X, SAG3, SRS9, BSR4, SPA, and MIC were analyzed for CD8⁺ T cell epitopes based on predicted binding affinity to HLA-A03 supertype molecules using ARB algorithms from immunoepitope database (IEDB) http://www.immuneepitope.org/. A total of 34 unique peptides $IC_{50} < 50$ nM of all ranked nonameric peptides were selected. All protein sequences were from ToxoDB 5.1.

Quantitative assays to measure binding of peptides to HLA class I molecules are based on inhibition of binding of radiolabeled standard peptide. Assays were as described in Sidney, J., et al. Immunome Res 4, 2 (2008). Concentration of peptide yielding 50% inhibition of binding of radiolabeled probe peptide ($IC_{50}$) was calculated. Under conditions used, where [radiolabeled probe]<[MHC] and $IC_{50} \geq$ [MHC], measured $IC_{50}$ values are reasonable approximations of true $K_d$ values.

Statistical Analyses

Statistical analyses for all in vitro assays were performed using 2-tailed student's T test. Two-tailed P values<0.05 were considered statistically significant. Peptides were considered immunogenic in mice if they induced IFN-γ spot formation from immunized mice that were significant (P<0.05) compared with spot formation from control mice. All mouse experiments were repeated at least twice, with 4-5 mice for each group.

III. Peptides and Adjuvants

HLA-B*0702-restricted peptides—$GRA7_{20-28}$ (LPQFA-TAAT (SEQ ID NO: 8)) and $GRA3_{27-35}$ (VPFVVFLVA (SEQ ID NO: 9)), PADRE (AKFVAAWTLKAAA (SEQ ID NO: 7)) and Pam₂Cys (Pam₂-KSS) (18) were synthesized by Synthetic Biomolecules, San Diego at >90% purity in lyophilized form. The TLR4 agonist was a MLA mimetic that was synthesized by the Infectious Diseases Research Institute (IDRI, Seattle, Wash.).

Mice

Female HLA-B*0702 transgenic mice express a chimeric HLA-B07/H2-$D^b$ MHC Class I molecule, are on a C57BL/6 background and have been previously described (11), which were produced at Pharmexa-Epimmune (San Diego, Calif.) and bred at the University of Chicago. All studies were conducted with the approval of the Institutional Animal Care and Use Committee at the University of Chicago.

Analysis of Peptide Solubility

Peptides were dissolved in PBS followed by brief vortexing, to give a concentration of 5 mg/ml. Samples were centrifuged at 15,000 rpm at room temperature for 1 h. Supernatant concentrations were determined by measuring absorbance at 280 nm and Bradford assay. The percentage solubility of the samples was calculated.

Immunizations and Challenge

HLA-B*0702 mice were inoculated subcutaneously (s.c.) at the base of the tail using a 30-gauge needle with single peptides or a mixture of two of the identified B7 CD8⁺ T cell peptides, (amino acid sequence LPQFATAAT (SEQ ID NO: 8) [LT9] and amino acid sequence VPFVVFLVA (SEQ ID NO: 9) [VA9]) (50 μg of each peptide per mouse), with or without 50 μg PADRE and 50 μg Pam₂Cys emulsified in 20 μg of MLA (TLR4 agonist). Control mice were injected with PBS. Mice were boosted twice at 2-week intervals with a total of 50 μg of each peptide per mouse with each immunogen. For challenge studies, mice were challenged 14 days post immunization with peptide emulsions via intraperitoneal (i.p.) inoculation with Prugniaud—a type II strain luciferase expressing parasite.

ELISPOT Assay

Mice were euthanized 10 to 14 days after the last immunization. Spleens were harvested, pressed through a 70 μm screen to form a single-cell suspension, and depleted of erythrocytes with AKC lysis buffer (160 mM $NH_4Cl$, 10 mM $KHCO_3$, 100 μM EDTA). Murine ELISPOT assays were performed using anti-mouse IFN-γ mAb (AN18) and the biotinylated anti-mouse IFN-γ mAb (R4-6A2) and $5 \times 10^5$ splenocytes were plated per well. All antibodies and reagents used for the ELISPOT assay were obtained from Mabtech (Cincinnati, Ohio). Cells were plated in at least 3 replicate wells for each condition. Results were expressed as the number of spot forming cells (SFCs) per $10^6$ murine splenocytes. Murine splenocytes were incubated with the relevant blocking antibody for 1.5 to 2 h at 37° C. and 5% $CO_2$ before they were seeded at $5 \times 10^5$ cells per well. Anti-CD4⁺ antibody (RM4-5, BioLegend), anti-CD8 monoclonal antibody (53-6.7, BD Biosciences), and their relevant isotype control (Rat $IgG_{2a}$, BD Biosciences) were added to each sample at a final concentration of 10 μg/ml. To assay for B7-restricted IFN-γ production, splenocytes were incubated with 0.5 μg of FC BLOCK™ (BD Biosciences) per $10^6$ cells for 10-15 min at 4° C. and washed before anti-HLA-B*0702 (BioLegend) mAb or its isotype control (mouse $IgG_{2a}$, BioLegend) was added at a final concentration of 20 μg/ml.

T Cell Proliferation Assay

A splenocyte suspension containing $5 \times 10^6$ cells/ml from immunized mice was plated into 96-well U-bottomed tissue culture plates (100 µl per well) along with 100 µl of each stimulant diluted to appropriate concentrations in complete RPMI1640. The stimulant used was peptide at 10 µg/ml. Concanavalin A at 10 µg/ml was used as a positive control and cells cultured with media alone were used as negative controls. The plates were incubated for 3 days in 5% CO2 at 37° C. and pulsed with 1 µCi [$^3$H] thymidine per well for the final 18 h. The cells were then harvested onto a unifilter 96-well plate using a cell harvester (Packard Instrument, Meriden, Conn.). After drying, 25 µl of MICROSCINT™ was added to each well and the filter plate was sealed and counted in a Top Count (Packard Instrument) to determine radioactivity incorporated into DNA. Results are expressed as the stimulation index (SI), calculated as the ratio between the mean counts per minute (cpm) for triplicate stimulated cultures and the mean counts per min for triplicate unstimulated cultures. SI values 2.0-fold greater than the SI of the control groups were considered to be significant.

In Vivo Bioluminescence Imaging

The transgenic *T. gondii* strain used for in vivo challenges was derived from the type II Prugniaud (Pru) strain and expresses the Firefly luciferase (FLUC) gene constitutively by tachyzoites and bradyzoites. Mice infected with Pru-FLUC tachyzoites were imaged at 5 days post-challenge using the in vivo imaging system (IVIS; Xenogen, Alameda, Calif.) as previously described. Mice were injected i.p. with 200 µl of D-luciferin (15.4 mg/ml) and immediately anesthetized in an O$_2$-rich induction chamber with 2% isoflurane. After 12 min, mice were imaged in ventral positions and photonic emissions were assessed using Living Image® 2.20.1 software (Xenogen). Data were presented as pseudo-color representations of light intensity and mean photons/s/region of interest (ROI).

MHC-Peptide Binding Assays

Quantitative assays to measure the binding of peptides to HLA Class I molecules are based on the inhibition of binding of a radiolabeled standard peptide. Assays were performed as follows: 1 to 10 nM concentrations of radiolabeled peptides were coincubated with 1 M to 1 nM concentration of purified MHC in the presence of 1 to 3 uM human $\beta_2$-microglubulin. After 2 days, the binding of radiolabeled peptide to the corresponding MHC Class I molecule was determined by capturing MHC-peptide complexes on Greiner Lumitrac 600 microplates coated with the W6/32 antibody. The bound counts per minutes was measured using a Topcount microscintillation counter and the concentration of peptide yielding 50% inhibition of the binding of the radiolabeled probe peptide (IC$_{50}$) was calculated. Under the conditions used, where [radiolabeled probe]<[MHC] and IC$_{50}$≥[MHC], the measured IC$_{50}$ values are reasonable approximations of the true $K_d$ values.

Statistical Analyses

There were 3-5 mice per group. PBMC were obtained from 3 seropositive and 4 seronegative donors. Each experiment was repeated at least twice. Statistical analyses for all in vitro assays were performed using a 2-tailed student's T-test. Two-tailed P values<0.05 were considered to be statistically significant. Peptides were considered immunogenic in mice if they induced IFN-γ spot formation or proliferation SI from immunized mice that was significant (P<0.05) compared with spot formation from control mice.

TABLE 1

Binding affinity of identified peptides and immunogenicity in human and transgenic mice

| Peptides (a) | Peptide sequences | SEQ ID NO: | Predicted IC50 nM (b) | Affinity (c) HLA-A*0201 | Elicit IFN-γ (d) in seropositive human | Elicit IFN-γ (d) in seronegative human | Immunogenicity (e) in mice |
|---|---|---|---|---|---|---|---|
| GRA6$_{24-32}$ | VVFVVFMGV | 1 | 76.3 | 14 | + | − | − |
| GRA6$_{29-37}$ | FMGVLVNSL | 2 | 26.6 | 18 | + | − | + |
| GRA3$_{25-33}$ | FLVPFVVFL | 3 | 8.6 | <0.10 | + | − | + |
| SAG2C$_{38-46}$ | FLSLSLLVI | 11 | 34.1 | 736 | + | − | + |
| SAG2D$_{180-189}$ | FMIAFISCFA | 12 | 15.6 | 32 | + | − | + |
| SAG2X$_{44-52}$ | FVIFACNFV | 16 | 4.5 | 34 | + | − | + |
| SAG2X$_{351-359}$ | FMIVSISLV | 13 | 27.5 | 16 | + | − | + |
| SAG3$_{375-383}$ | FLLGLLVHV | 15 | 2.3 | 6.40 | + | − | + |
| SAG3$_{136-144}$ | FLTDYIPGA | 14 | 2.8 | 0.70 | + | − | + |
| SPA$_{12-20}$ | ITMGSLFFV | 17 | 10.7 | 0.16 | + | − | + |
| SPA$_{82-90}$ | GLAAVVAV | 18 | 27.8 | 9.60 | + | − | + |
| MIC1$_{9-17}$ | VLLPVLFGV | 20 | 7.3 | 1.70 | + | − | + |
| MICA2/P$_{11-19}$ | FAAAFFPAV | 19 | 12.5 | 1.40 | + | − | − |

(a) Peptides derived from proteins and the position within the proteins.
(b) Peptides binding affinity to HLA-A02 were predicted using the ARB algorithms from immunoepitope database (IEDB).
(c) Binding affinity was determined by MHC binding assay.
(d) PBMC cells from four *T. gondii*-seropositive HLA-A02 humans and four seronegative ones were stimulated with peptides, the T cells that produce IFN-γ were tested by ELISPOT assay.
(e) Splenic T cells were isolated from HLA-A*0201 mice 10-14 days after peptide immunization and tested for their ability to generate IFN-γ in response to peptide.

TABLE 2

Peptides utilized for screening CD8+ T cells (a) Predicted peptide candidates
(b) MHC binding affinity for HLA-A03 supertype

| a HLA-A*1101 | ANTIGEN | PEPTIDE SEQUENCES | SEQ ID NO: | LENGTH | LOCATION | PREDICTED IC$_{50}$ nM | POOL |
|---|---|---|---|---|---|---|---|
| HLA-A*1101 | GRA15 | STSPFATRK | 24 | 9 | 152-160 | 5 | P1 |
| HLA-A*1101 | GRA15 | ASTSPFATRK | 25 | 10 | 150-159 | 18.2 | |
| HLA-A*1101 | GRA10 | AAAATPGLPK | 26 | 10 | 568-577 | 9 | |
| HLA-A*1101 | GRA10 | AAATPGLPK | 27 | 9 | 569-577 | 13.2 | |
| HLA-A*1101 | GRA10 | GVPAVPGLLK | 28 | 10 | 507-516 | 17 | |
| HLA-A*1101 | GRA10 | SVVEENTMAK | 29 | 10 | 865-874 | 25.1 | |
| HLA-A*1101 | SAG2C | STFWPCLLR | 21 | 9 | 13-21 | 9.3 | P2 |
| HLA-A*1101 | SAG2C | ALLDHVFIEK | 30 | 10 | 231-240 | 11.9 | |
| HLA-A*1101 | SAG2C | SSPQNIFYK | 31 | 9 | 290-298 | 12.9 | |
| HLA-A*1101 | SAG2C | STTGVGETGK | 32 | 10 | 163-172 | 28.4 | |
| HLA-A*1101 | SAG2C | GTEYSLALK | 33 | 9 | 136-144 | 35.4 | |
| HLA-A*1101 | SAG2D | SSPQNIFYK | 34 | 9 | 122-130 | 12.9 | |
| HLA-A*1101 | SAG2D | ALLEHVFIEK | 35 | 10 | 1:63-72 | 20.2 | P3 |
| HLA-A*1101 | SAG2D | SSAQTFFYK | 36 | 9 | 290-298 | 1.8 | |
| HLA-A*1101 | SAG2D | TVYFSCDPK | 37 | 9 | 154-162 | 5.3 | |
| HLA-A*1101 | SAG2D | PSSAQTFFYK | 38 | 10 | 289-298 | 17.9 | |
| HLA-A*1101 | SAG3 | VVGHVTLNK | 39 | 9 | 80-88 | 15.4 | |
| HLA-A*1101 | SAG3 | KQYWYKIEK | 40 | 9 | 145-153 | 19.3 | |
| HLA-A*1101 | SRS9 | TTCSVLVTVK | 41 | 10 | 357-366 | 20.6 | P4 |
| HLA-A*1101 | SRS9 | AAASVQVPLK | 42 | 10 | 140-149 | 29.9 | |
| HLA-A*1101 | SRS9 | AIQSQKWTLK | 43 | 10 | 169-178 | 35 | |
| HLA-A*1101 | BSR4 | TTRFVEIFPK | 44 | 10 | 284-293 | 10.3 | |
| HLA-A*1101 | BSR4 | VSGSLTLSK | 45 | 9 | 83-91 | 21.1 | |
| HLA-A*1101 | SPA | SSAYVFSVK | 22 | 9 | 250-258 | 9.3 | P5 |
| HLA-A*1101 | SPA | TSSAYVFSVK | 46 | 10 | 249-258 | 12.2 | |
| HLA-A*1101 | SPA | YVFSVKELPK | 47 | 10 | 253-262 | 18 | |
| HLA-A*1101 | SPA | KTEATYCYK | 48 | 9 | 262-270 | 18.4 | |
| HLA-A*1101 | SPA | MTLMITRDSK | 49 | 10 | 195-204 | 25.5 | |
| HLA-A*1101 | SPA | AVVSLLRLLK | 23 | 10 | 89-98 | 6.5 | |
| HLA-A*1101 | SPA | VVSLLRLLK | 50 | 9 | 90-98 | 7.2 | |
| HLA-A*1101 | MIC1 | LTLTFISTK | 51 | 9 | 338-346 | 13.8 | P6 |
| HLA-A*1101 | MIC3 | SVQLGSFDK | 52 | 9 | 32-40 | 12.9 | |
| HLA-A*1101 | MIC4 | SAVWFGVAK | 53 | 9 | 16-24 | 17.2 | |
| HLA-A*1101 | MICA2P | GVMTPNQMVK | 54 | 10 | 63-72 | 14.3 | |

| b PEPTIDE SEQUENCE | SEQ ID NO: | LENGTH | PROTEIN | POSITION | HLA-A03-SUPERTYPE | | | | | | SUPERTYPE ALLELES BOUND |
|---|---|---|---|---|---|---|---|---|---|---|---|
| | | | | | HLA-A*0301 | HLA-A*1101 | HLA-A*3001 | HLA-A*3101 | HLA-A*3301 | HLA-A*6801 | |
| STFWPCLLR | 21 | 9 | SAG2C | 13-21 | 22 | 10 | 1272 | 1.2 | 3.4 | 0.97 | 5 |
| SSAYVFSVK | 22 | 9 | SPA | 250-258 | 12 | 10 | 1826 | 97 | 181 | 2.1 | 5 |
| AVVSLLRLLK | 23 | 10 | SPA | 89-98 | 17 | 34 | 8.1 | 1296 | 1100 | 94 | 4 |

TABLE 3

Peptides, their affinity for HLA-*1101, and their immunogenicity in humans and for transgenic mice.

| Peptide Sequences | SEQ ID NO: | Protein[a] | Affinity[b] HLA-A*1101 | Elicit IFN-γ[c] in Seropositive human | Elicit IFN-γ[c] in Seronegative human | Immunogenicity[d] in mice |
|---|---|---|---|---|---|---|
| KSFKDILPK | 4 | SAG1$_{224-232}$ | 54 | + | − | + |
| AMLTAFFLR | 5 | GRA6$_{164-172}$ | 3.6 | + | − | + |
| RSFKDLLKK | 6 | GRA7$_{134-142}$ | 14 | + | − | − |
| STFWPCLLR | 21 | SAG2C$_{13-21}$ | 10 | + | − | + |

TABLE 3-continued

Peptides, their affinity for HLA-*1101, and their immunogenicity in humans and for transgenic mice.

| Peptide Sequences | SEQ ID NO: | Protein[a] | Affinity[b] HLA-A*1101 | Elicit IFN-γ[c] in Seropositive human | Elicit IFN-γ[c] in Seronegative human | Immunogenicity[d] in mice |
|---|---|---|---|---|---|---|
| SSAYVFSVK | 22 | SPA$_{250-258}$ | 10 | + | − | + |
| AVVSLLRLLK | 23 | SPA$_{89-98}$ | 34 | + | − | + |

[a] Peptides derived from proteins and the position within the proteins
[b] Binding affinity was performed by MHC binding assay.
[c] PBMC from four T gondii-seropositive HLA-A03 supertype persons and four seronegative persons were stimulated with peptides, the T cell that produce IFN-γ were tested by ELISpot assay.
[d] Splenic T cell were isolated from HLA-A*03 supertype (which includes the HLA-A*1101 haplotype) mice 10 to 14 days after peptide immunization and tested for their ability to generate IFN-γ in response to peptide

TABLE 4

| Peptides (a) | Peptide sequences | SEQ ID NO: | Predicted IC50 nM (b) | Affinitiy (c) HLA*B0702 | Solubility (d) in PBS (%) | Elicit IFN-γ (d) in seropositive human | Elicit IFN-γ (d) in seronegative human | Immunogenicity (e) in mice | Protective in mice |
|---|---|---|---|---|---|---|---|---|---|
| GRA7$_{20-28}$ | LPQFATAAT | 8 | 62.4 | 14 | 99 | + | − | + | + |
| GRA3$_{27-35}$ | VPFVVFLVA | 9 | 373.9 | 18 | 10 | + | − | − | − |

(a) Peptides derived from 2 proteins and the position within the protein.
(b) Peptide-binding affinities to HLA-B*0702 were predicted using the ARB algorithms from the immunoepitope database (IEDB). IC50 is 50% inhibition of binding by a competitor.
(c) Binding affinity was performed by MHC-binding assay.
(d) Percentage solubility, values are determined by absorbance at 280 nm and Bradford assay.
(e) PBMC cells from 4 T gondii-seropositive HLA-B07 humans and 3 seronegative ones were stimulated with GRA720-28 (LPQFATAAT (SEQ ID NO: 8)) and GRA327-35 (VPFVVFLVA (SEQ ID NO: 9)); the T cells that produce IFN-γ were tested by ELISPOT assay.
(f) Splenic T cells were isolated from HLA-A*0702 mice 2 weeks after peptide immunization and tested for their ability to generate IFN-γ in response to peptide. (−), Not immunogenic at any dose.
(g) Protective HLA-B*0702 in transgenic mice.

PUBLICATIONS CITED

These publications are incorporated by reference to the extent they relate materials and methods disclosed herein.

Bui et al. (2007) BMC Bioinformants 8:361.
Cheng Y et al. (1973) Biochem. Pharmacol. 22:3099-3108.
Cong H et al. (2011) Hum Immunol. October 12.
Cong H et al. (2010) Immunome Res. December 3; 6:12.
Cong H et al. (2011) Vaccine. January 17; 29(4):754-62. Epub 2010 Nov. 21.
Dzierszinski et al. (2000) Mol. Microbiol. 37:574-82.
Gulukota K et al. (1997) J. Mol. Biol. 267:1258-1267.
Henriquez F L, et al. Trends Parasitol. 2010 November; 26(11):550-5. Epub January 26.
Hill D, et al. (2011) J Parasitol. April; 97(2):328-37. Epub March 3.
Jung C. et al. (2004) Int. J. Parasitol. 34:285-396.
Kim, S. K. et al. 92007) Infect. Immun. 75:1626-1634.
Kubo R T et al. (1994) J Immunol; 152:3913-24.
Mercier C. et al. (2005) Int. J. Parasitol. 35:829-849.
Padilla A., et al. (2007) Infect. Immun. 75:231-235.
Rapin N, et al. (2010) 5:e9862.
Saeij J P, et al. (2008) Infect Immun; 76:2402-10.
Sette A, et al. (1994) J Immunol 1994; 153:5586-92;
Tan T G, et al. (2010) Vaccine May 21; 28(23):3977-3989. Epub March 26.
Vita R. et al. (2010) Nucleic Acids Res. (January Database Issue): D854-62. Epub (Nov. 11, 2009).
Witola W H, et al. (2011) Infect Immun. February; 79(2):756-66. Epub November 22.

The invention claimed is:

1. A composition comprising a plurality of peptides, wherein the plurality of peptides comprises a first peptide with the amino acid sequence KSFKDILPK (SEQ ID NO: 4), a second peptide with the amino acid sequence RSFKDLLKK (SEQ ID NO: 6), and a third peptide with the amino acid sequence AKFVAAWTLKAAA (SEQ ID NO: 7), wherein the plurality of peptides are linked to form a chimeric polypeptide.

2. The composition of claim 1, wherein the composition comprises an oil-in-water emulsion that includes a synthetic adjuvant monophosphorvl lipid A (MLA).

3. The composition of claim 1 wherein the plurality of peptides further comprises one or more of AVVSLLRLLK (SEQ ID NO:23), STFWPCLLR (SEQ ID NO:21), and SSAYVFSVK (SEQ ID NO:22).

4. The composition of claim 3, further comprising an adjuvant.

5. The composition of claim 3 wherein the plurality of peptides further comprises one or more of FLSLSLLVI (SEQ ID NO: 11) FMIAFISCFA (SEQ ID NO: 12), FVIFACNFV (SEQ ID NO: 16), FMIVSISLY (SEQ ID NO: 13), FLLGLLVHV (SEQ ID NO: 15), FLTDYIPGA (SEQ ID NO: 14), ITMGSLFFV (SEQ ID NO: 17), GLAAAVYAV (SEQ ID NO: 18), VLLPVLFGV (SEQ ID NO: 20), FAAAFFPAV (SEQ ID NO: 19), VVFVVFMGV (SEQ ID NO: 1), FMGVLVNSL (SEQ ID NO: 2), FLVPFVVFL (SEQ ID NO: 3), AMLTAFFLR (SEQ ID NO: 5), LPOFATAAT (SEQ ID NO: 8), VPFVVFLVA (SEQ ID NO: 9), and HF10 (HPGSVNEFDF (SEQ ID NO: 10)).

6. The composition of claim 5, further comprising an adjuvant.

7. The composition of claim 1 wherein the plurality of peptides further comprises one or more of FLSLSLLVI (SEQ ID NO: 11), FMIAFISCFA (SEQ ID NO: 12), FVIFACNFV (SEQ ID NO: 16), FMIVSISLV (SEQ ID NO: 13), FLLGLLVHV (SEQ ID NO: 15), FLTDYIPGA (SEQ ID NO: 14), ITMGSLFFV (SEQ ID NO: 17), GLAAAVVAV (SEQ ID NO: 18), VLLPVLFGV (SEQ ID NO: 20), FAAAFFPAV (SEQ ID NO: 19), VVFVVFMGV (SEQ ID NO: 1), FMGVLVNSL (SEQ ID NO: 2), FLVPFVVFL (SEQ ID NO: 3), AMLTAFFLR (SEQ ID NO: 5), LPQFATAAT (SEQ ID NO: 8), VPFVVFLVA (SEQ ID NO: 9), and HF10 (HPGSVNEFDF (SEQ ID NO: 10)).

8. The composition of claim 7, further comprising an adjuvant.

9. The composition of claim 1 further comprising an adjuvant.

\* \* \* \* \*